(12) United States Patent
Faulkner et al.

(10) Patent No.: US 8,932,314 B2
(45) Date of Patent: Jan. 13, 2015

(54) PRIME AND FIRE LANCING DEVICE WITH CONTACTING BIAS DRIVE AND METHOD

(75) Inventors: Allan James Faulkner, Avoch (GB); Nicholas Foley, Edinburgh (GB); David Colin Crosland, Edinburgh (GB); Matthew James Young, Edinburgh (GB); Paul Trickett, Hamilton (GB)

(73) Assignee: LifeScan Scotland Limited, Inverness (GB)

( * ) Notice: Subject to any disclaimer, the term of this patent is extended or adjusted under 35 U.S.C. 154(b) by 774 days.

(21) Appl. No.: 12/435,967

(22) Filed: May 5, 2009

(65) Prior Publication Data
US 2009/0281458 A1 Nov. 12, 2009

Related U.S. Application Data

(60) Provisional application No. 61/052,069, filed on May 9, 2008.

(51) Int. Cl.
- *A61B 17/32* (2006.01)
- *A61B 5/151* (2006.01)
- *A61B 5/15* (2006.01)

(52) U.S. Cl.
CPC ........... *A61B 5/1411* (2013.01); *A61B 5/15186* (2013.01)
USPC ....................................... 606/182

(58) Field of Classification Search
USPC .................. 606/182, 183, 172; 600/583, 167
See application file for complete search history.

(56) References Cited

U.S. PATENT DOCUMENTS

| 4,462,405 A | 7/1984 | Ehrlich |
| 4,469,110 A | 9/1984 | Slama |
| 4,895,147 A | 1/1990 | Bodicky et al. |
| 4,976,724 A | 12/1990 | Nieto et al. |
| 5,147,375 A | 9/1992 | Sullivan et al. |
| 5,207,699 A | 5/1993 | Coe |
| 5,318,584 A | 6/1994 | Lange et al. |
| 5,324,303 A | 6/1994 | Strong et al. |
| 5,350,392 A | 9/1994 | Purcell et al. |
| 5,423,847 A | 6/1995 | Strong et al. |
| 5,554,166 A | 9/1996 | Lange et al. |
| 5,628,764 A | 5/1997 | Schraga et al. |

(Continued)

FOREIGN PATENT DOCUMENTS

| EP | 1652474 A | 5/2006 |
| JP | 5-95937 A | 4/1993 |

(Continued)

OTHER PUBLICATIONS

International Search Report issued in related International Application No. PCT/GB2009/001145, dated Aug. 4, 2009, 9 pages.

(Continued)

*Primary Examiner* — Ryan Severson
*Assistant Examiner* — Anh Dang

(57) ABSTRACT

Described and illustrated herein is an exemplary lancing device. The lancing device includes a first housing, second housing, movable member, lancet, and lancet depth adjustment member. The lancet depth adjustment member is captured by both the first and second housings so that the lancet depth adjustment member is rotatable relative to both housings to provide for a plurality of stop surfaces to the movable member. Other exemplary embodiments are also described.

37 Claims, 27 Drawing Sheets

(56) References Cited

U.S. PATENT DOCUMENTS

| | | |
|---|---|---|
| 5,868,772 A | 2/1999 | LeVaughn et al. |
| 5,964,718 A | 10/1999 | Duchon et al. |
| 6,045,567 A | 4/2000 | Taylor et al. |
| 6,080,172 A | 6/2000 | Fujiwara et al. |
| 6,197,040 B1 | 3/2001 | LeVaughn et al. |
| 6,558,402 B1 | 5/2003 | Chelak et al. |
| 6,723,111 B2 | 4/2004 | Abulhaj et al. |
| 6,840,912 B2 | 1/2005 | Kloepfer et al. |
| 6,929,650 B2 | 8/2005 | Fukuzawa et al. |
| 7,025,774 B2 | 4/2006 | Freeman et al. |
| 7,153,318 B2 | 12/2006 | Marshall et al. |
| 2003/0050655 A1 | 3/2003 | Roe |
| 2003/0187470 A1 | 10/2003 | Chelak et al. |
| 2004/0034318 A1 | 2/2004 | Fritz et al. |
| 2004/0267229 A1 | 12/2004 | Moerman et al. |
| 2005/0125017 A1 | 6/2005 | Kudrna et al. |
| 2005/0125019 A1 | 6/2005 | Kudrna et al. |
| 2005/0234492 A1 | 10/2005 | Tsai et al. |
| 2006/0052809 A1 | 3/2006 | Karbowniczek et al. |
| 2006/0100655 A1 | 5/2006 | Leong et al. |
| 2006/0100656 A1* | 5/2006 | Olson et al. .............. 606/181 |
| 2006/0247671 A1 | 11/2006 | LeVaughn |
| 2007/0055297 A1 | 3/2007 | Fukuzawa et al. |
| 2007/0055298 A1 | 3/2007 | Uehata et al. |
| 2007/0083222 A1 | 4/2007 | Schraga |
| 2007/0173875 A1 | 7/2007 | Uschold |
| 2007/0173876 A1 | 7/2007 | Aylett et al. |
| 2007/0255300 A1 | 11/2007 | Vanhiel et al. |
| 2008/0039885 A1 | 2/2008 | Purcell |
| 2008/0039886 A1 | 2/2008 | Shi |
| 2008/0188883 A1 | 8/2008 | Deck et al. |
| 2008/0228212 A1 | 9/2008 | List |
| 2009/0036916 A1 | 2/2009 | Fukuzawa et al. |
| 2009/0093832 A1 | 4/2009 | Fukuzawa |
| 2009/0143810 A1 | 6/2009 | Kitamura et al. |
| 2009/0275860 A1 | 11/2009 | Nakamura et al. |
| 2009/0299398 A1 | 12/2009 | Yoritaka et al. |
| 2010/0294447 A1 | 11/2010 | Farrar et al. |
| 2011/0082459 A1 | 4/2011 | Aravot |

FOREIGN PATENT DOCUMENTS

| | | |
|---|---|---|
| JP | H0716218 A | 1/1995 |
| JP | H07275223 A | 10/1995 |
| JP | H10328168 A | 12/1998 |
| JP | 2000237172 A | 9/2000 |
| JP | 2000262498 A | 9/2000 |
| JP | 2001523508 A | 11/2001 |
| JP | 2002503119 A | 1/2002 |
| JP | 2004512129 A | 4/2004 |
| JP | 2004344291 A | 12/2004 |
| JP | 2005505325 A | 2/2005 |
| JP | 2005124998 A | 5/2005 |
| JP | 2005-253781 A | 9/2005 |
| JP | 2005305155 A | 11/2005 |
| JP | 2005312763 A | 11/2005 |
| JP | 2006136716 A | 6/2006 |
| JP | 3134339 U | 8/2007 |
| JP | 2007190394 A | 8/2007 |
| JP | 2008086357 A | 4/2008 |
| JP | 2008220957 A | 9/2008 |
| JP | 2011507988 A | 3/2011 |
| JP | 2011519659 A | 7/2011 |
| WO | 9743962 A1 | 11/1997 |
| WO | 2006109452 A1 | 10/2006 |
| WO | WO 2006/116441 A1 | 11/2006 |
| WO | WO 2006/132504 A1 | 12/2006 |
| WO | 2007006399 A1 | 1/2007 |
| WO | WO 2007/006399 A1 | 1/2007 |
| WO | 2007037207 A1 | 4/2007 |
| WO | 2007102576 A1 | 9/2007 |
| WO | 2007105617 A1 | 9/2007 |
| WO | WO 2007/130830 A | 11/2007 |
| WO | WO 2007130830 A2 * | 11/2007 |
| WO | 2007145102 A1 | 12/2007 |

OTHER PUBLICATIONS

Written Opinion issued in related International Application No. PCT/GB2009/001145, dated Aug. 4, 2009, 10 pages.

* cited by examiner

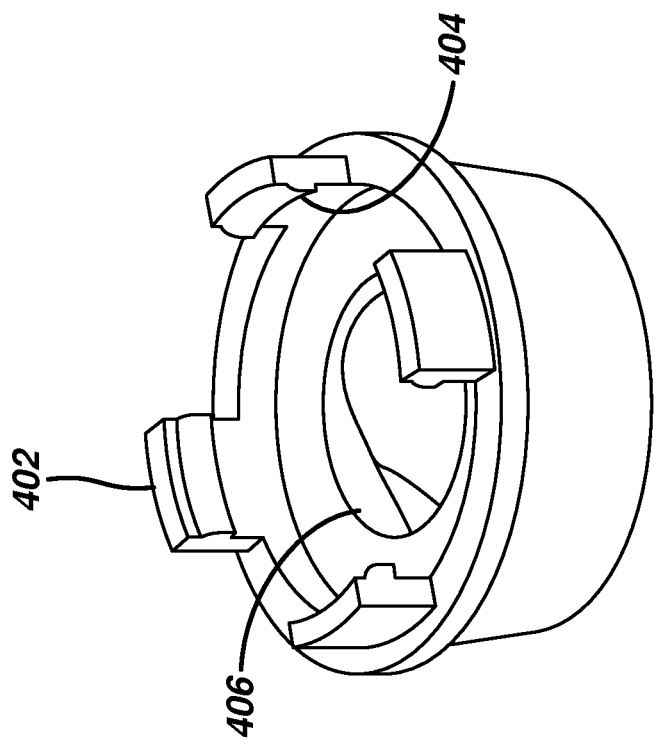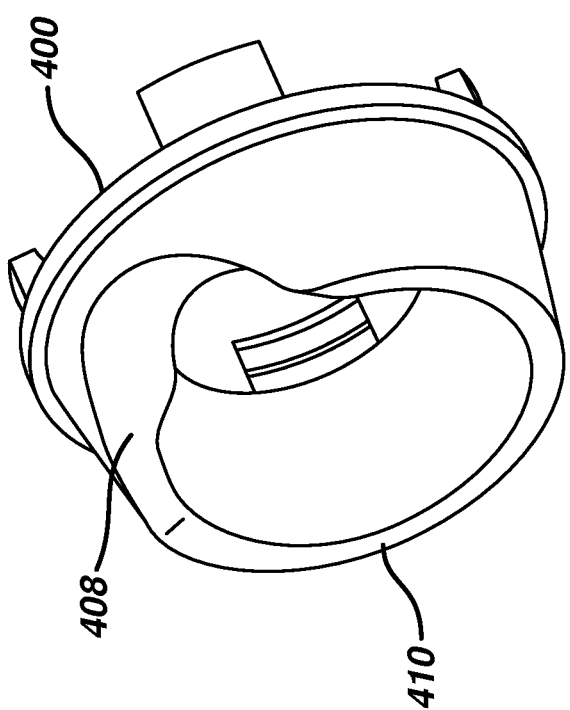
FIG. 4

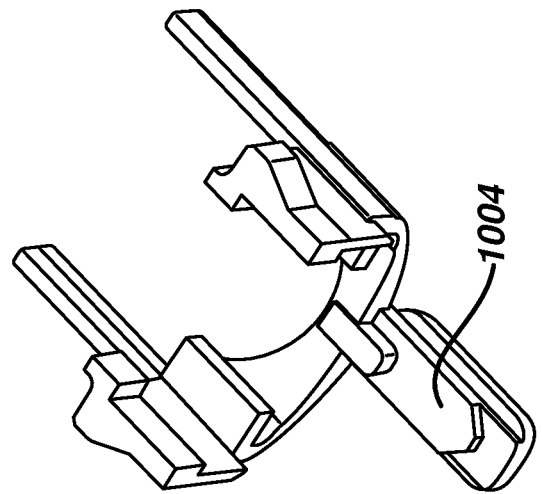
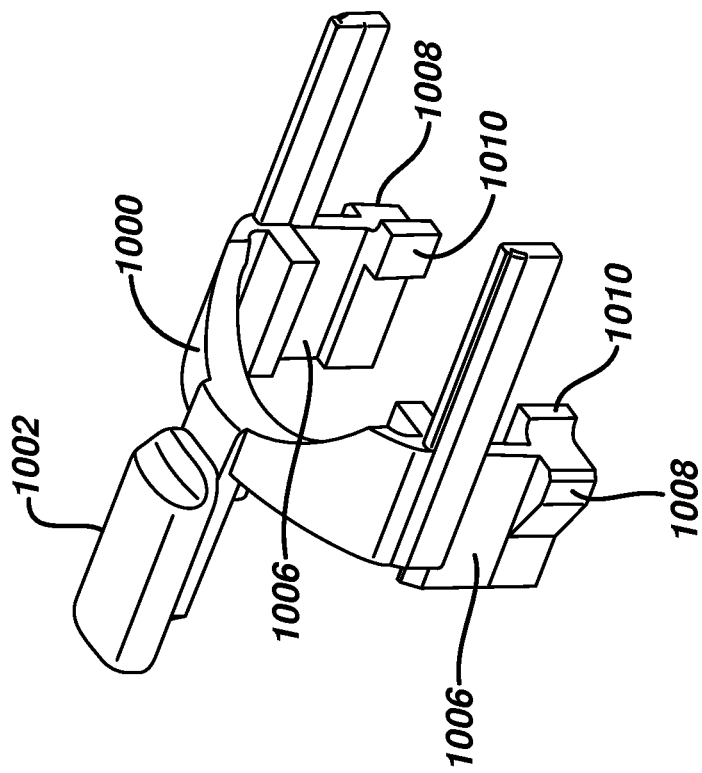
FIG. 10

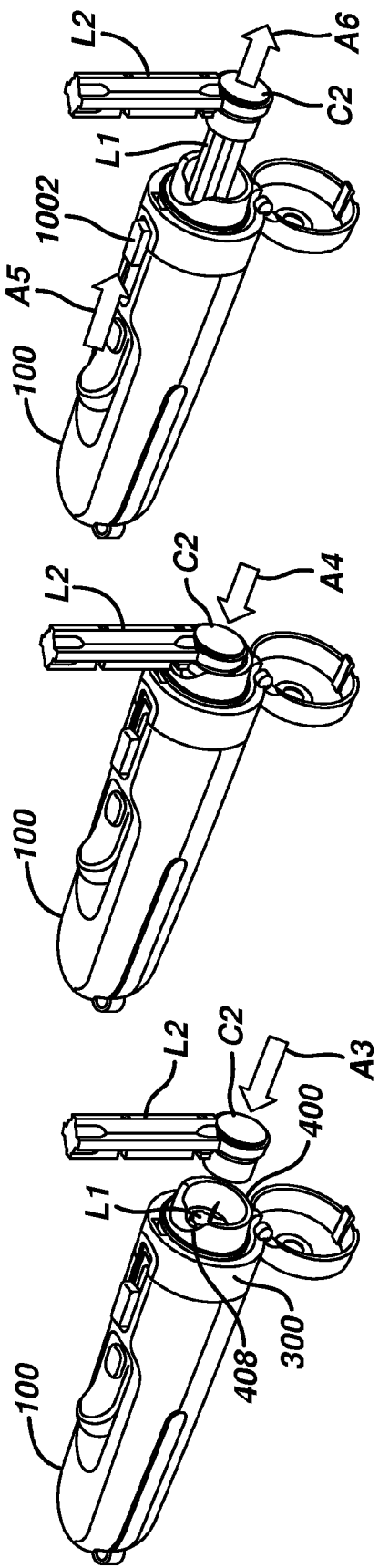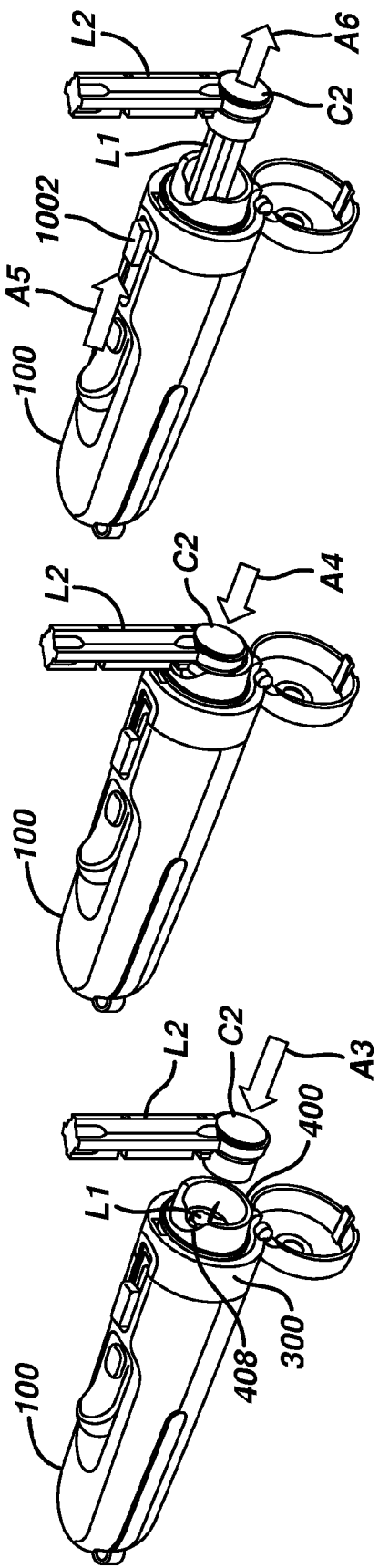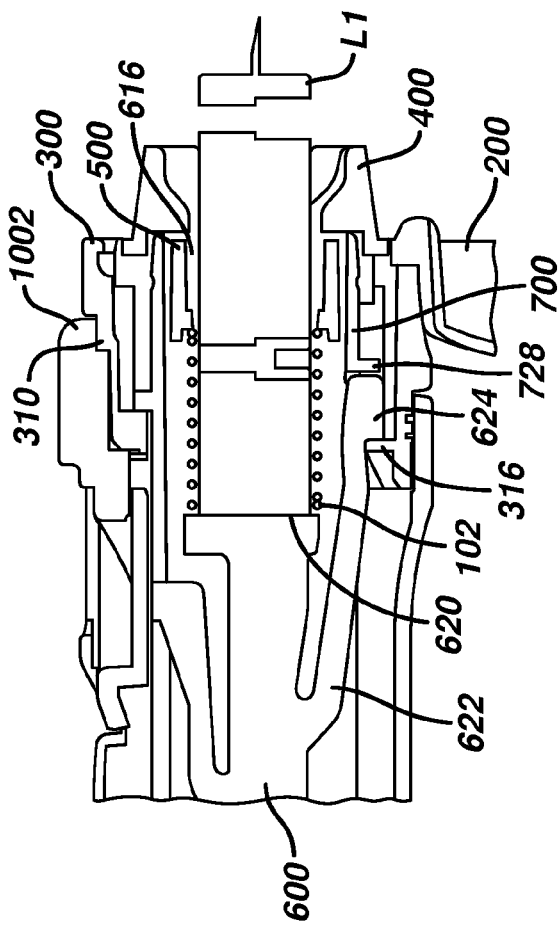

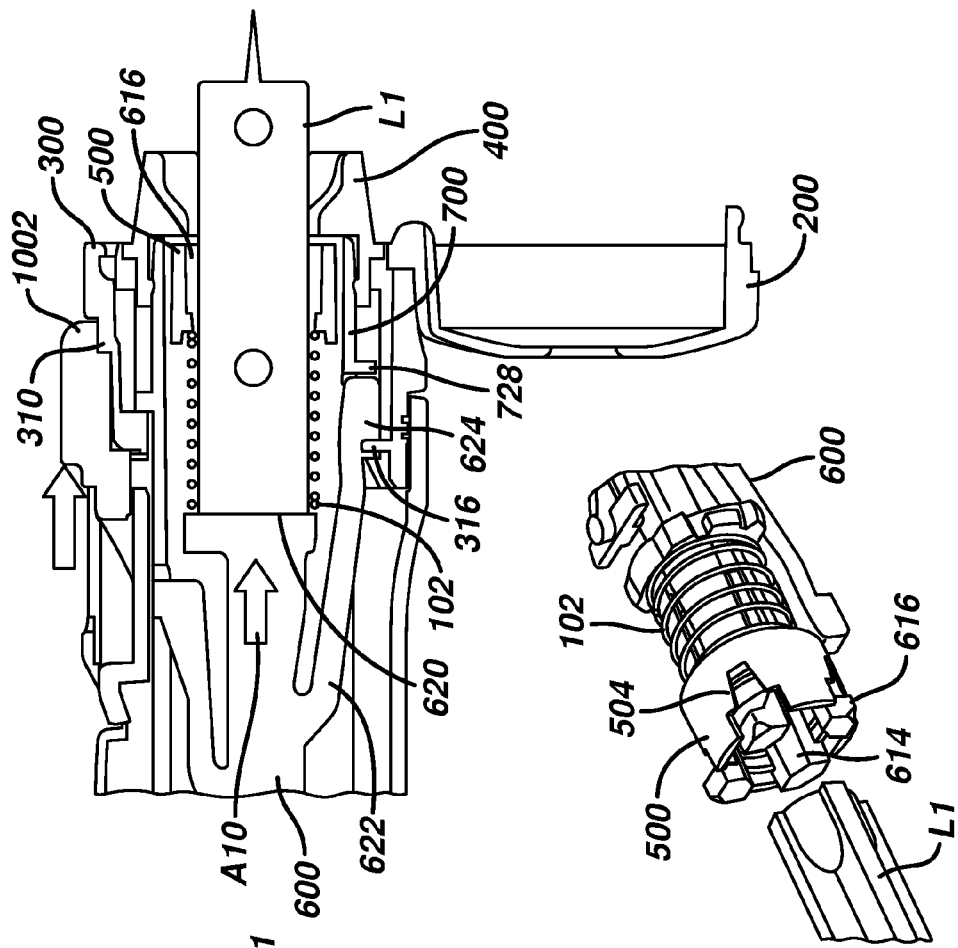
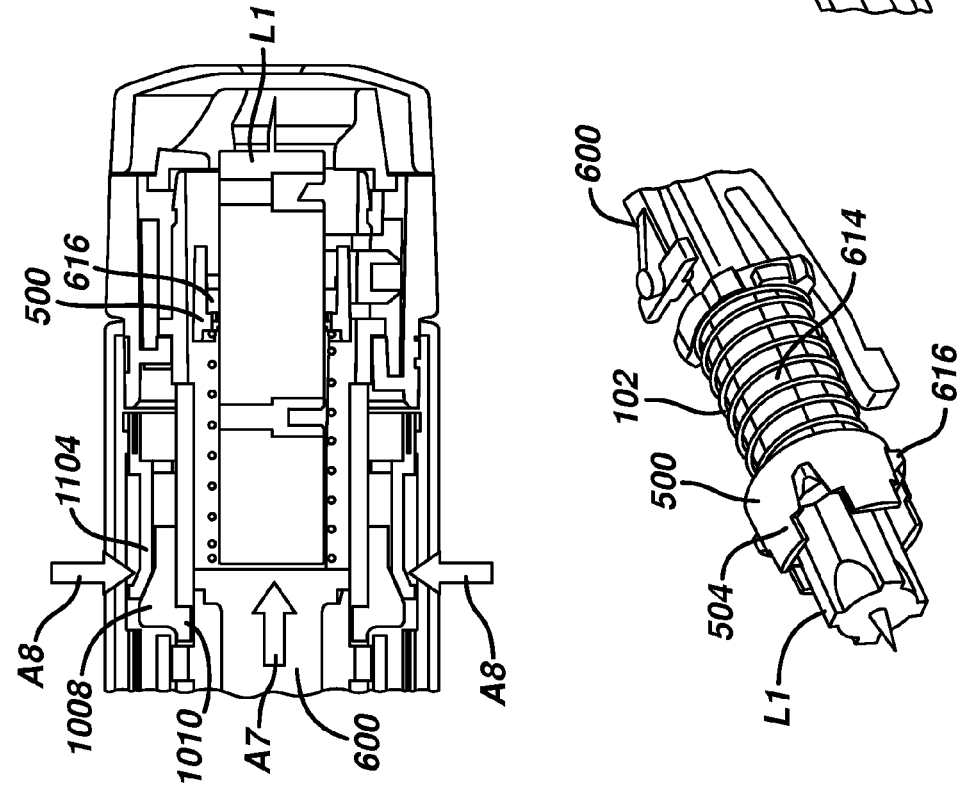

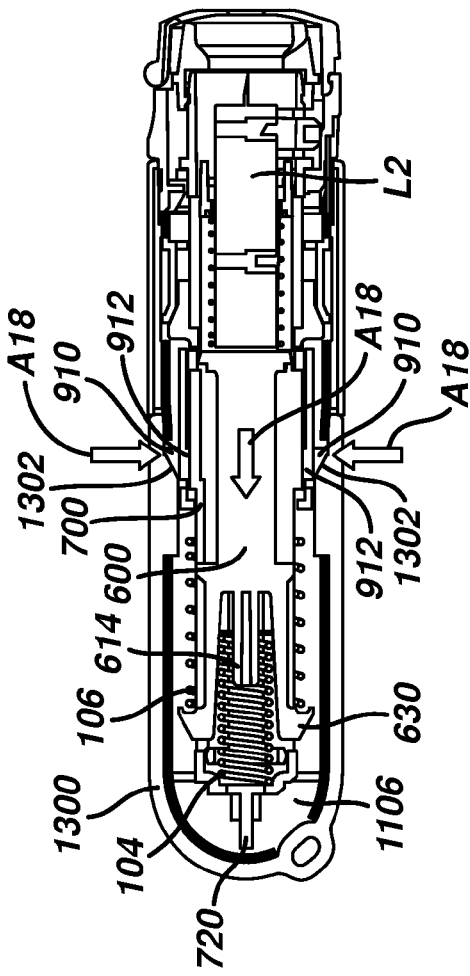
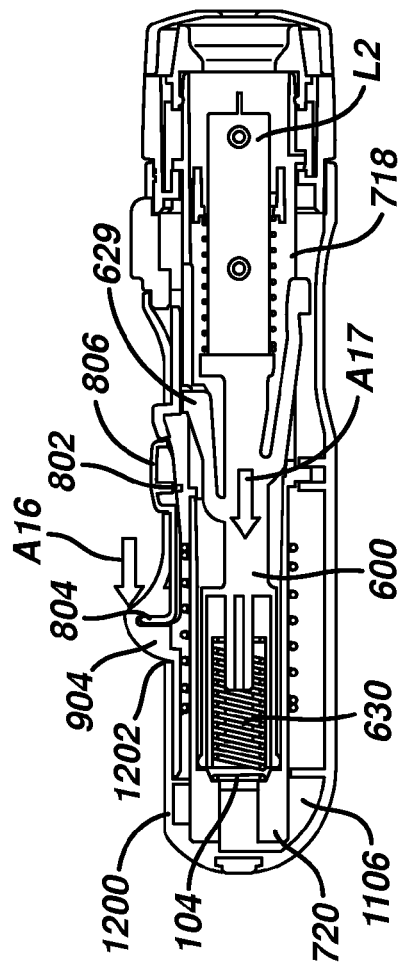
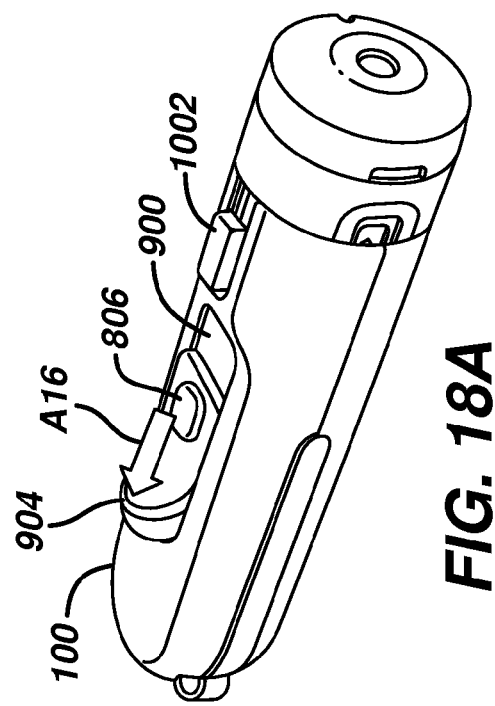
FIG. 18B
FIG. 18C
FIG. 18A

PRIME AND FIRE LANCING DEVICE WITH CONTACTING BIAS DRIVE AND METHOD

PRIORITY

This application claims the benefits of priority of U.S. Provisional Patent Application Ser. No. 61/052,069 filed on May 9, 2008.

BACKGROUND

Conventional lancing devices generally have a rigid housing, various operating mechanisms and a lancet that can be armed and launched so as to briefly protrude from one end of the lancing device. For example, conventional lancing devices can include a lancet that is mounted within a rigid housing such that the lancet is movable relative to the rigid housing along a longitudinal axis thereof. Typically, the lancet is spring loaded and launched, upon release of the spring, to penetrate (i.e., "lance") a target site (e.g., a dermal tissue target site). A bodily fluid sample (e.g., a whole blood sample) can then be expressed from the penetrated target site for collection and analysis.

Conventional lancing devices typically require a user to arm the lancing device, urge the lancing device against a target site, and then press a button or other switch to manually activate the lancing device such that a lancet within the device is launched (also referred to as "fired") towards the target site. The lancet then penetrates (e.g., lances) the target site, thereby creating an opening for the expression of a bodily fluid sample.

The arming and launching of conventional lancing devices involves a multitude of complicated mechanisms that result in the lancing device being relatively large in size, costly to manufacture and cumbersome to operate. In addition, the operation of conventional lancing device mechanisms can induce both vibrations within the lancing device and sounds that increase the level of pain perceived by a user.

SUMMARY OF THE DISCLOSURE

Applicants have recognized a need for a lancing device that is relatively inexpensive to manufacture and easily operated. Such device must also produce a minimal amount of vibration and/or sound during use, thereby decreasing the level of pain perceived by a user.

In accordance with one aspect, there is provided a lancing device that includes a first housing, second housing, movable member, lancet, and lancet depth adjustment member. The first housing has spaced apart proximal and distal ends disposed along a longitudinal axis. The second housing is disposed in the first housing in a fixed relationship with the first housing. The movable member is disposed in the second housing and configured for movement along the longitudinal axis and in the first housing. The lancet is coupled to the movable member. The lancet depth adjustment member is captured by both the first and second housings so that the lancet depth adjustment member is rotatable relative to both housings to provide for a plurality of stop surfaces to the movable member.

In yet another aspect, a lancing device is provided that includes a first housing, second housing, movable member, bias member, first actuator, second actuator, and a lance. The first housing has spaced apart proximal and distal ends disposed along a longitudinal axis. The second housing is disposed in the first housing in a fixed relationship with the first housing. The movable member is disposed in the second housing and configured for movement along the longitudinal axis in the first housings. The bias member is located in the second housing to bias the moveable member in a direction towards the distal end. The first actuator is coupled to the movable member so that the movable member is positioned proximate the proximal end in a primed-position. The second actuator is carried on a portion of the first actuator, the second actuator configured to allow the movable member to move from the primed-position to a position proximate the distal end. The lancet is coupled to the movable member.

In yet a further aspect, a lancing device is provided that includes a housing, a lancet, a movable member, and a collet. The housing has spaced apart proximal and distal ends disposed along a longitudinal axis. The lancet has a body and a lancing projection, at least the body being disposed in the housing. The movable member is disposed in the housing and configured for movement along the longitudinal axis. The moveable member includes a plurality of arms extending away from the longitudinal axis. The collet is mounted on the plurality of arms for movement of the collet along the longitudinal axis on the plurality of arms from a first position of the collet in which the plurality of arms constrains the body of the lancet from movement and a second position of the collet in which the body of the lancet is free to move without constraint by the plurality of arms.

In an embodiment, the lancing device further includes: a first bias member located in the second housing to bias the moveable member in a direction towards the distal end; a first actuator coupled to the movable member so that the movable member is positioned proximate the proximal end in a prime position; and a second actuator carried on a portion of the first actuator, the second actuator configured to allow the movable member to move from the prime position to a position proximate the distal end.

In an embodiment, the moveable member has a plurality of arms extending away from the longitudinal axis towards the distal end; and the lancing device further includes: a collet mounted on the plurality of arms for movement of the collet along the longitudinal axis on the plurality of arms from a first position of the collet in which the plurality of arms constrains the body of the lancet from movement and a second position of the collet in which the body of the lancet is free to move without constraint by the plurality of arms.

In an embodiment, the lancing device further includes a lancet ejection mechanism including a third actuator mounted to the first housing. The third actuator being disposed in: a first position in which the third actuator is disengaged from both the lancet depth adjustment member and the moveable member, and a second position in which the third actuator is connected to the moveable member with the depth adjustment member in a specific position so that a portion of the third actuator is displaced partially in a groove formed on a circumferential portion of the depth adjustment member to move the moveable member towards the distal end to eject the lancet.

In an embodiment, the lancing device further includes: a collar disposed between the depth adjustment member and the collet, the collar configured to prevent movement of the collet towards the distal end.

In an embodiment, the lancing device further includes: a cap to cover an aperture in which the lancet can extend from the depth adjustment member, the cap being connected to the depth adjustment member.

In an embodiment, the first housing includes two halves connected together.

In an embodiment, the second housing includes a unitary member connected to a positioning band coupled to the first housing, the second housing having at least one groove that extends through the unitary member along the longitudinal axis to allow communication from the inside of the second housing to the inside of the first housing.

In an embodiment, the lancing device further includes: a second bias member configured to bias the moveable member in a direction towards the proximal end.

In an embodiment, the moveable member includes at least one return arm that extends through the groove so that the moveable member is guided by the at least one return arm along a path defined by a groove.

In an embodiment, the second bias member includes a helical spring disposed outside the second housing and connected to the at least one return arm.

In an embodiment, the lancing device further includes: a third bias member coupled to the moveable member to bias the collet in a direction towards the distal end.

In an embodiment, the first bias member is selected from a group consisting of springs, magnets, or combinations thereof.

In an embodiment, the second bias member is selected from a group consisting of springs, magnets, or combinations thereof.

In yet another aspect, a method of operating a lancet can be achieved translating, via a hand, a movable member disposed inside a housing along a longitudinal axis in a first direction to a prime position in which the movable member is locked into a prime position against a force biasing the moveable member in a second direction opposite the first direction; unlocking, with the same hand, the moveable member from the prime position to allow the biasing force to cause the moveable member to move a lancet constrained to the moveable member in the second direction towards a target site; rotating a collar about the housing with the same hand until a groove is aligned with an ejection actuator; and moving, with the same hand, the ejection actuator into the groove to move the moveable member into a position in which the lancet is no longer constrained to the moveable member.

In yet a further aspect, a lancing device is provided that includes first and second housings, a moveable member, and a depth adjustment member. The first housing has spaced apart proximal and distal ends disposed along a longitudinal axis. The second housing is disposed in the first housing in a fixed relationship with the first housing. The movable member is disposed in the second housing and configured for movement along the longitudinal axis. The lancet depth adjustment member limits a travel of the movable member along the longitudinal axis towards the distal end. The lancet depth adjustment member is captured by both the first and second housings so that the lancet depth adjustment member is rotatable relative to both housings to provide for a plurality of stop surfaces to the movable member.

In yet a further aspect, a lancing device is provided that includes first and second housings, a moveable member, a lancet, and a collet. The first housing has spaced apart proximal and distal ends disposed along a longitudinal axis. The second housing is disposed in the first housing in a fixed relationship with the first housing. The movable member is disposed in the second housing and configured for movement along the longitudinal axis. The movable member is disposed in the second housing and configured for movement along the longitudinal axis. The moveable member includes a plurality of arms extending away from the longitudinal axis towards the distal end. The lancet has a body and a projection extending from the body of the lancet, the body of the lancet capable of being disposed in a volume defined by the plurality of arms of the moveable member. The collet is mounted on the plurality of arms for movement of the collet along the longitudinal axis on the plurality of arms from a first position of the collet in which the plurality of arms constrains the body of the lancet from movement and a second position of the collet in which the body of the lancet is not constrained by the plurality of arms.

These and other embodiments, features and advantages will become apparent to those skilled in the art when taken with reference to the following more detailed description of the invention in conjunction with the accompanying drawings that are first briefly described.

BRIEF DESCRIPTION OF THE FIGURES

The accompanying drawings, which are incorporated herein and constitute part of this specification, illustrate presently preferred embodiments of the invention, and, together with the general description given above and the detailed description given below, serve to explain features of the invention (wherein like numerals represent like elements), of which:

FIG. 4 illustrates two perspective views of a collar, according to an embodiment described and illustrated herein.

FIG. 10 illustrates two perspective views of a third actuator, according to an embodiment described and illustrated herein.

FIGS. 15A-15E illustrate a sequence of steps used in capping a lancet in a lancing device, according to an embodiment described and illustrated herein.

FIGS. 16A-16F include detailed cross sectional and perspective views of a lancing device before and after a lancet is ejected, according to an embodiment described and illustrated herein.

FIGS. 18A-18E illustrate a sequence of steps used in priming a lancing device, according to an embodiment described and illustrated herein.

DETAILED DESCRIPTION OF THE FIGURES

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
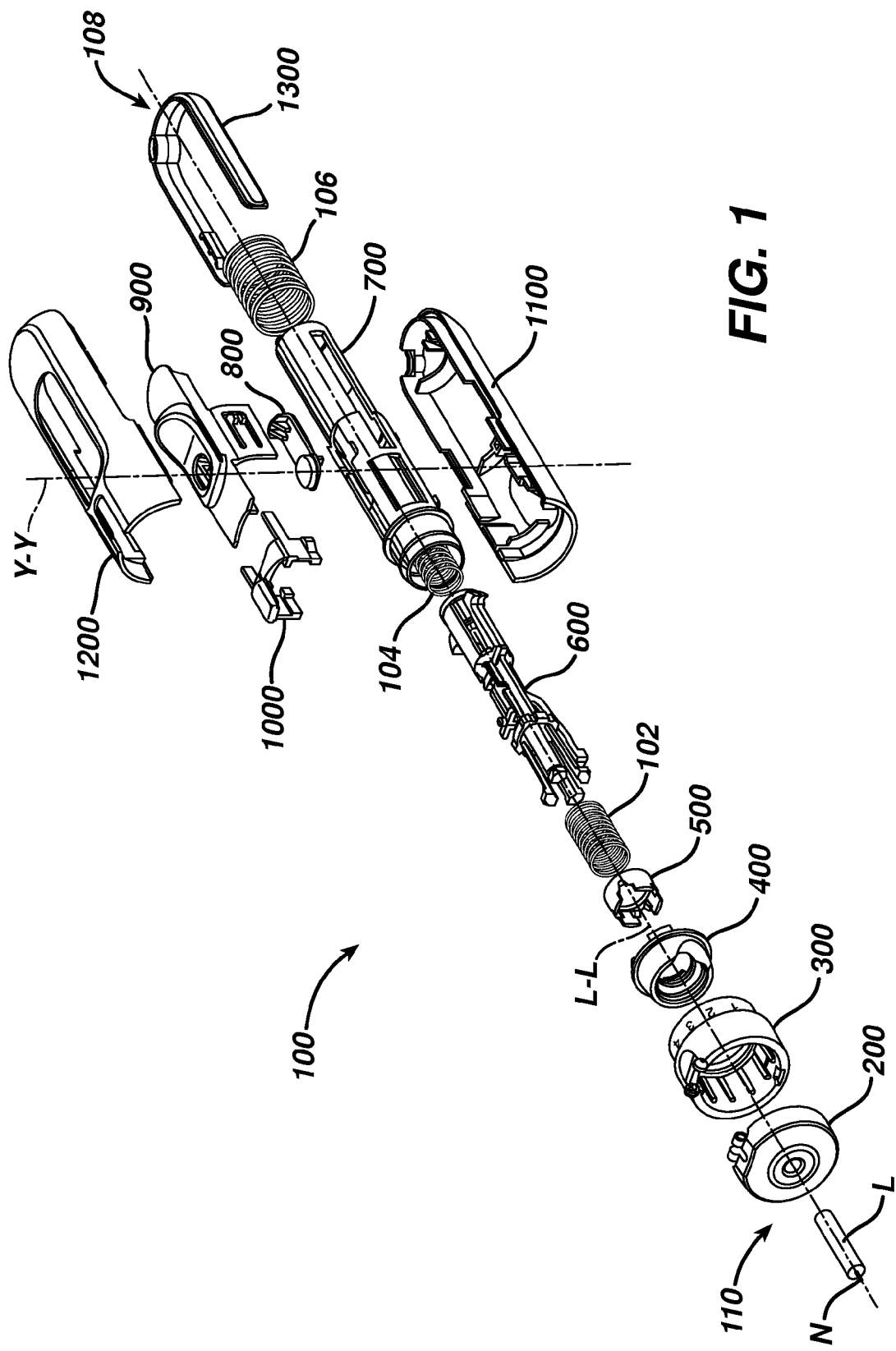
FIG. 1 is an exploded view of a lancing device, according to an embodiment described and illustrated herein.

FIG. 1 is an exploded view of a lancing device 100, according to an embodiment described and illustrated herein. Lancing device 100 includes cap 200, lancet depth adjustment member 300 (which can also be referred to as a depth adjuster), collar 400 (which can also be referred to as a shroud), collet 500, third bias member 102 (which can also be referred to as a collet spring), movable member 600 (which can also be referred to as a holder), first bias member 104 (which can also be referred to as a launch spring), second housing 700 (which can also be referred to as a chassis), second bias member 106 (which can also be referred to as a return spring), second actuator 800 (which can also be referred to as a firing assembly), first actuator 900 (which can also be referred to as a priming assembly), third actuator 1000 (which can also be referred to as an eject assembly), first housing bottom 1100, first housing top 1200, and band 1300. Lancing device 100 includes a proximal end 108 and a distal end 110, which includes first housing top 1200 on the top side, and first housing bottom 1100 on the bottom side. As used herein, the term "proximal" indicates a position closest to the hand of the user or operator and the term "distal" indicates a position spaced apart and away from the user or operator in normal operation of the lancing device. Also, as used herein, the term "collet" represents a collar and in some embodiments, can also be configured as a split cone type device similar to those used to hold workpieces but is not in any manner limited to this configuration.

When assembled, second housing 700, first housing bottom 1100, first housing top 1200, and band 1300 are fixedly attached to each other, while cap 200, lancet depth adjustment member 300, collar 400, collet 500, third bias member 102, movable member 600, first bias member 104, second bias member 106, second actuator 800, first actuator 900, and third actuator 1000 are coupled, but are free to move in accordance with the description provided herein.

As illustrated in FIG. 1, cap 200, lancet depth adjustment member 300, collar 400, collet 500, third bias member 102, movable member 600, second housing 700, second bias member 106, and band 1300 are assembled along an axis L-L running from lancing device proximal end 108 to lancing device distal end 110, while first housing top 1200, first actuator 900, third actuator 1000, second actuator 800, and first housing bottom 1100 are assembled along an axis Y-Y running perpendicular to an axis running from lancing device proximal end 108 to lancing device distal end 110. Cap 200, lancet depth adjustment member 300, collar 400, collet 500, third bias member 102, movable member 600, first bias member 104, second housing 700, second bias member 106, second actuator 800, first actuator 900, third actuator 1000, first housing bottom 1100, first housing top 1200, and band 1300 are generally snapped together, but can also be attached by a suitable technique such as, for example, screws, adhesives or thermal bonding, such as ultrasonic welding. In an embodiment, first housing top 1200, band 1300, and first housing bottom 1100 are attached using ultrasonic welding along their point of contact. Tight clearances are preferably maintained between the components of lancing device 100. In an embodiment, movable member 600 travels inside second housing 700 along an axis between lancing device proximal end 108 and lancing device distal end 110, with a clearance of approximately less than about 0.01 inches.

As described below, cap 200, lancet depth adjustment member 300, collar 400, collet 500, third bias member 102, movable member 600, first bias member 104, second housing 700, second bias member 106, second actuator 800, first actuator 900, third actuator 1000, first housing bottom 1100, first housing top 1200, and band 1300 are operatively connected such that a target site (e.g., a user's skin target site) can be lanced with a lancet (e.g., lancet L that includes lancet needle N) held within lancing device 100. In this regard, lancing device 100 is configured to launch lancet L such that lancet needle N lances a target site with first actuator 900 being configured to prime lancing device 100 prior to firing lancing device 100 (i.e., prior to launching lancet L), while second actuator 800 is configured to actuate the firing of lancing device 100. Furthermore, lancet depth adjustment member 300 is configured for a user to select a predetermined needle penetration depth into a target site.

Lancing device 100 can be any suitable size but can be beneficially sized to fit within the palm of a user's hand and has, therefore, a typical but non-limiting length in the range of 50 mm to 70 mm and a typical but non-limiting width in the range of about 10 mm to about 20 mm. Such a compact size is beneficial in that it requires less storage space and is less conspicuous than conventionally sized lancing devices.

Figure 2:
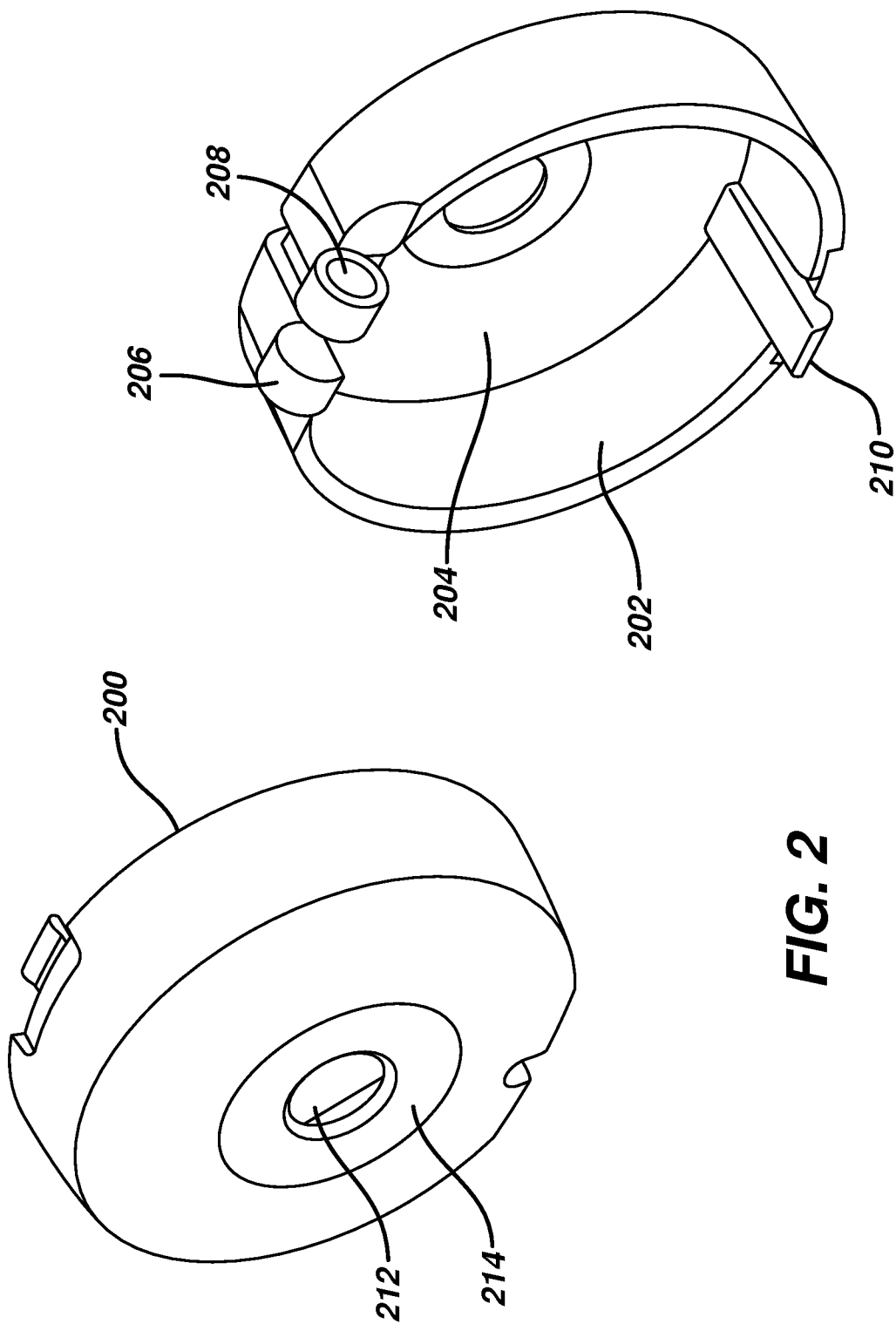
FIG. 2 is a perspective view of a cap, according to an embodiment described and illustrated herein.

FIG. 2 illustrates two perspective views of cap 200, according to an embodiment described and illustrated herein. Cap 200 includes wall 202, top 204, hinge 206, hinge pocket 208, latch 210, opening 212, and contour 214. Top 204 is connected along its perimeter to wall 202, and includes opening 212 and contour 214. Opening 212 allows lancet L to access a target site when it is launched. Contour 214 conforms to the target site, and enhances collection of sample from the target site. Hinge 206 includes hinge pocket 208 and allows cap 200 to be pivotally attached to lancet depth adjustment member 300. In an embodiment, hinge 206 can be temporarily removed from lancet depth adjustment member 300, i.e. for cleaning or replacement. Latch 210 can be used to removably fasten cap 200 to lancet depth adjustment member 300. Cap 200 can be at least partially clear or opaque, and can be made using rigid or flexible materials. For example, cap 200 can be injection molded using rigid thermoplastics, such as, for example, ABS, polycarbonate, acrylic, or polystyrene, or it can be injection or reaction injection molded using thermoplastic or thermosetting elastomers.

Figure 3:
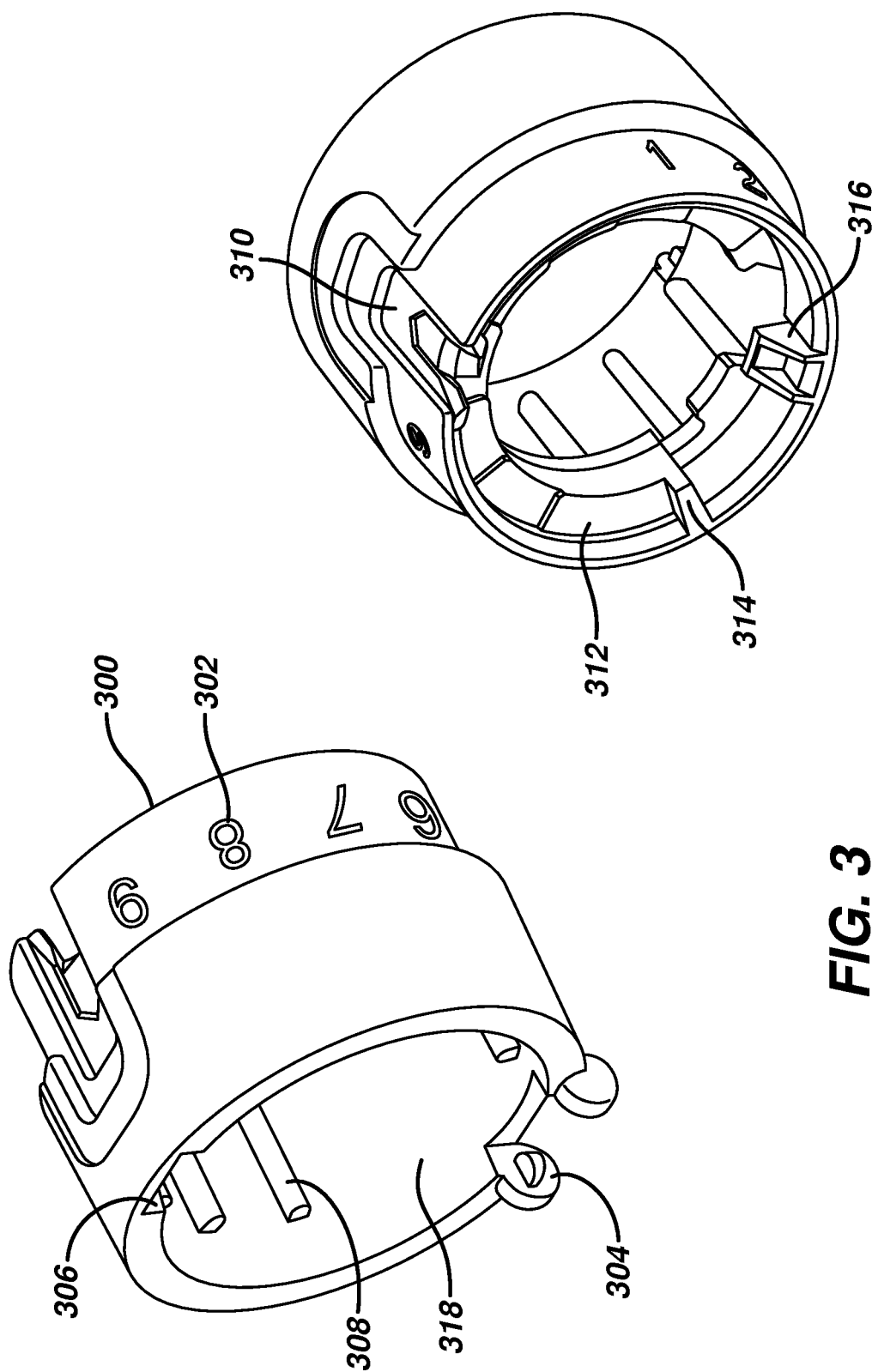
FIG. 3 illustrates two perspective views of a lancet depth adjustment member, according to an embodiment described and illustrated herein.

FIG. 3 illustrates two perspective views of lancet depth adjustment member 300, according to an embodiment described and illustrated herein. Lancet depth adjustment member 300 includes depth indicator 302, depth adjuster hinge 304, clasp 306, chassis engaging ribs 308, groove 310, depth stop 312, rotational stop 314, loading stop 316, and aperture 318. Depth indicator 302 includes a series of indicia, such as, for example, symbols, numerals or letters, and is correlated to lancet penetration depth. Depth indicator 302 can be etched, printed, or otherwise fixed to the surface of lancet depth adjustment member 300. Depth adjuster hinge 304 is used to attach lancet depth adjustment member 300 to cap 200, and typically mates with a feature on cap 200, such as, for example, hinge 206 and hinge pocket 208. Clasp 306 mates with a feature on cap 200, such as, for example, latch 210. Chassis engaging ribs 308 interact with features on second housing 700, positioning lancet depth adjustment member 300 at distinct rotational locations that correlate to depth indicator 302. As discussed in reference to FIG. 7, chassis engaging ribs 308 engage depth detent 726 of chassis or second housing 700, and position lancet depth adjustment member 300 at distinct rotational locations about the second housing 700. As lancet depth adjustment member 300 is rotated to distinct rotational locations (as indicated by depth indicator 302), depth stop 312 (of FIG. 3) is aligned to stop forward motion of movable member 600 (FIG. 6A) and lancet L when lancing device 100 is fired. Depth stop 312 includes a series of steps of increasing depth, as measured along axis L-L, correlating to depth indicator 302. Rotational stop 314 is connected to the final depth stop 312 and limits the rotation of depth indicator 302. Lancet depth adjustment member 300 includes groove 310. As is discussed later in respect to FIGS. 14-20, lancet depth adjustment member 300 is rotated to align groove 310 with depth window 1205 during the process of loading or unloading lancets into lancing device 100. When groove 310 is positioned for loading or unloading, loading stop 316 is positioned to stop motion of movable member 600 towards lancing device proximal end 108. Lancet depth adjustment member 300 can be at least partially clear or opaque, and can be made using a suitable rigid or flexible material. For example, lancet depth adjustment member 300 can be injection molded using rigid thermoplastics, such as, for example, ABS, polycarbonate, acrylic, or polystyrene, or it can be injection or reaction injection molded using thermoplastic or thermosetting elastomers.

FIG. 4 illustrates two perspective views of collar 400, according to an embodiment described and illustrated herein. Collar 400 includes positioning tabs 402, positioning ribs 404, opening 406, cutaway 408, and wall 410. Positioning tabs 402 includes positioning ribs 404, which interact with features on second housing 700 (FIG. 7), such as, for example, positioning groove 724. Positioning ribs 404 is disposed on second housing 700, allowing complete rotation about longitudinal axis L-L. Positioning ribs 404 and second housing 700 prevent linear travel along the axis that runs between lancing device proximal end 108 and lancing device distal end 110, fixing the position of collar 400 along that axis. Through opening 406 is defined by wall 410 to allow lancets to be loaded and unloaded into lancing device 100, and allows lancet L to travel towards the distal end when lancing device 100 is fired. Cutaway 408 in wall 410 allows a new lancet to be used as a cap holder, and as a lever when removing a cap from a new lancet, as described later in respect to FIGS. 15 and 17. Cutaway 408 can be positioned at any rotational angle, since collar 400 is free to rotate about second housing 700 while positioning ribs 404 travel in positioning groove 724. Another function of collar 400 is to prevent accidental needle contact when cap 200 is open. Needle N typically sits below the edge of wall 410, preventing a user from accidentally rubbing against needle N. Collar 400 can be at least partially clear or opaque, and can be made using rigid or flexible materials. For example, collar 400 can be injection molded using rigid thermoplastics, such as, for example, ABS, polycarbonate, acrylic, or polystyrene, or it can be injection or reaction injection molded using thermoplastic or thermosetting elastomers.

Figure 5:
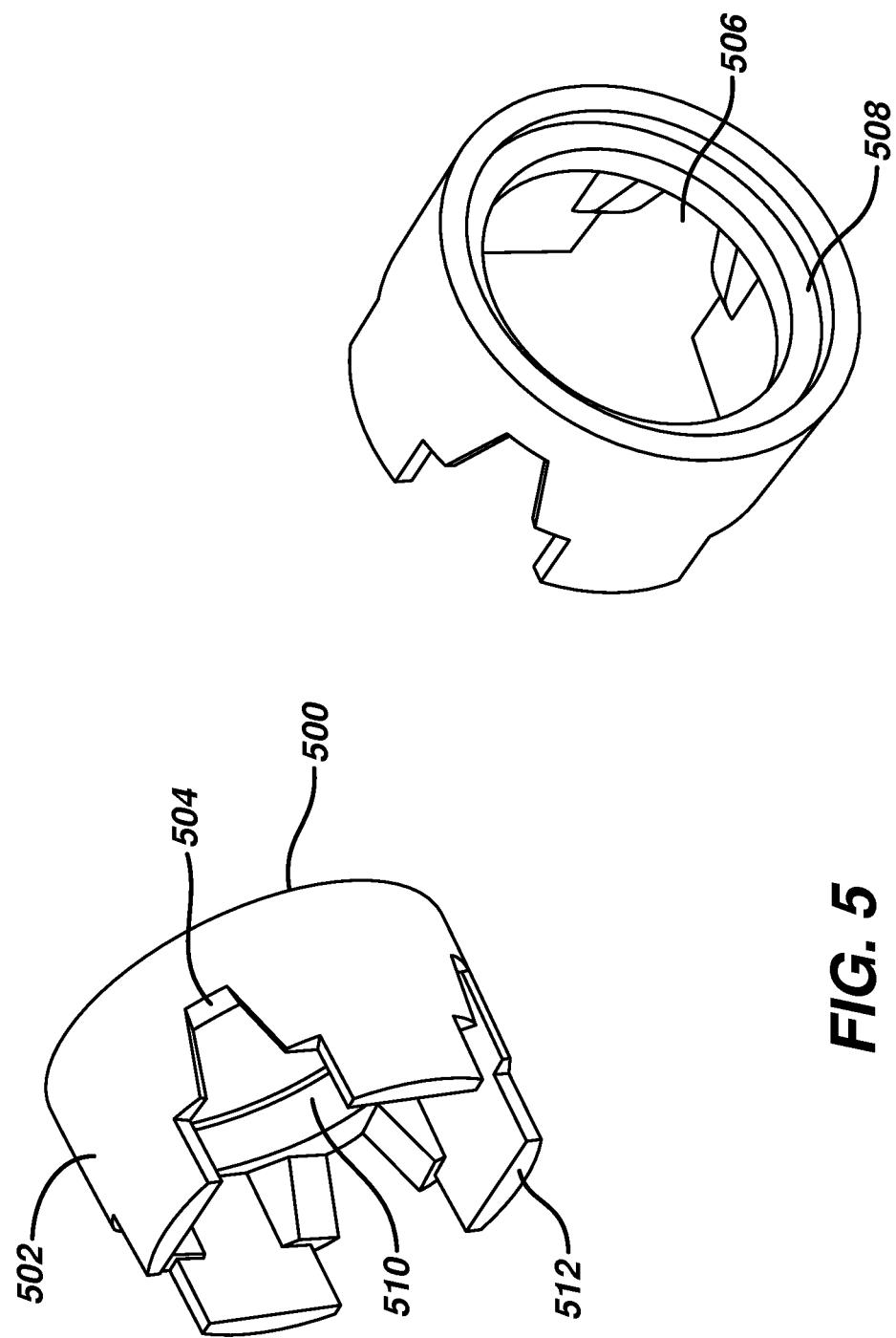
FIG. 5 illustrates two perspective views of a collet, according to an embodiment described and illustrated herein.

FIG. 5 illustrates two perspective views of collet 500, according to an embodiment described and illustrated herein. Collet 500 includes wall 502, positioning pockets 504, opening 506, spring support 508, contact surface 510, and forward stop 512. Collet 500 includes opening 506 and wall 502. Wall 502 forms forward stop 512 on its distal end, and includes a series of positioning pockets 504 along its surface. Forward stop 512 contacts a surface on collar 400, limiting its travel along the axis between lancing device proximal end 108 and lancing device distal end 110. Positioning pockets 504 mate with collet positioning tabs 616 completely when plurality of arms 614 grip lancet L, and partially when plurality of arms 614 loose grip with lancet L (as illustrated in FIG. 16). Contact surface 510 makes firm contact with plurality of arms 614 when gripping lancet L, and loosens its contact with plurality of arms 614 when loosening its grip on lancet L. Spring support 508 provides contact with third bias member 102, forcing collet 500 towards lancing device distal end 110 when third bias member 102 is at least partially compressed. Collet 500 can be at least partially clear or opaque, and can be made using rigid or flexible materials. For example, collet 500 can be injection molded using rigid thermoplastics, such as, for example, ABS, polycarbonate, acrylic, or polystyrene, or it can be injection or reaction injection molded using thermoplastic or thermosetting elastomers.

Figure 6:
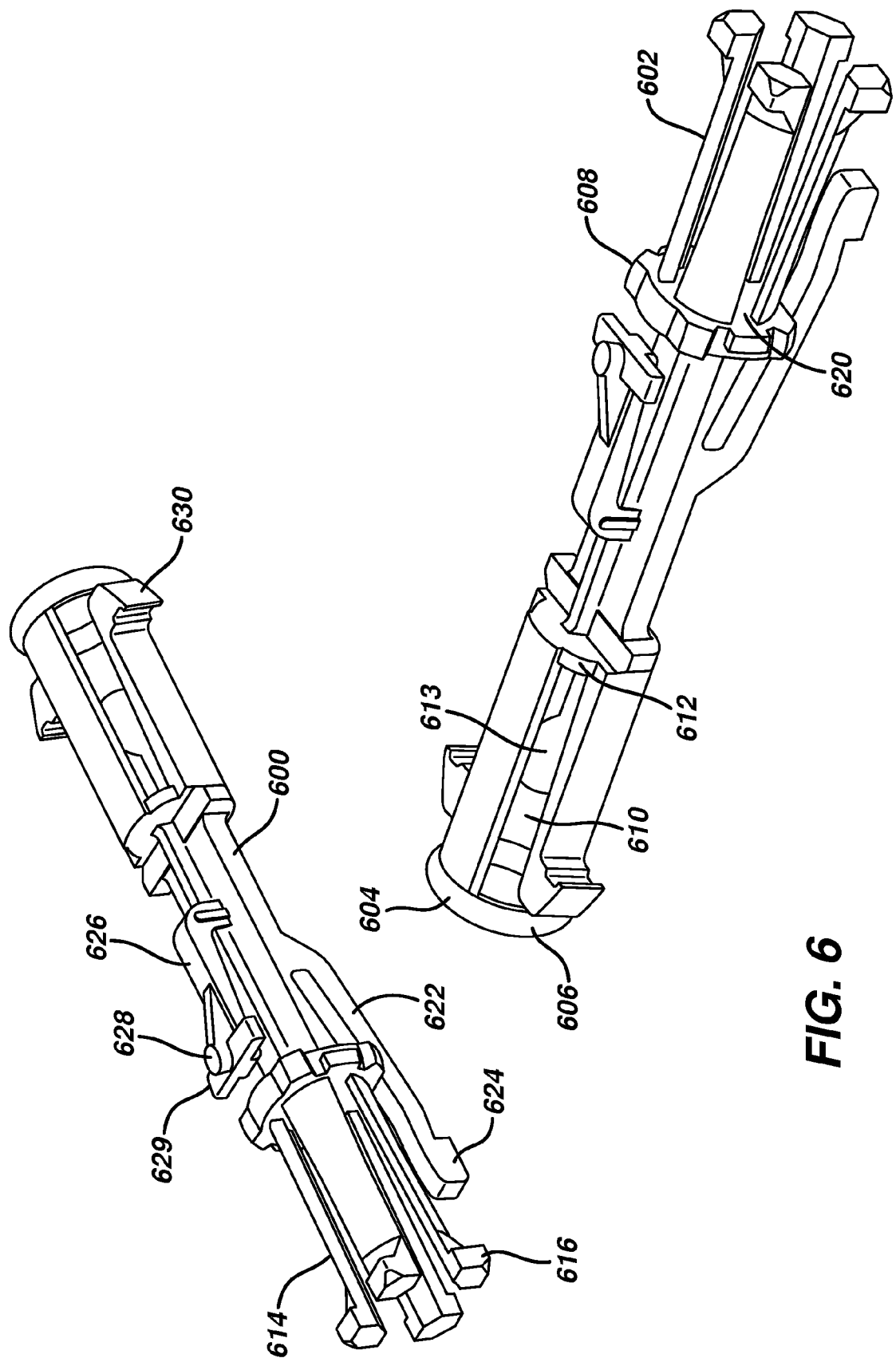
FIG. 6 illustrates two perspective views of a movable member, according to an embodiment described and illustrated herein.

FIG. 6 illustrates two perspective views of movable member 600, according to an embodiment described and illustrated herein. Movable member 600 includes distal end 602, proximal end 604, proximal bearing 606, distal bearing 608, launch spring housing 610, launch spring support 612, launch spring pin 613, plurality of arms 614, collet positioning tabs 616, collet spring support 620, stop arm 622, stop tip 624, firing arm 626, priming indicator 628, priming catch 629, and return arm 630. Proximal bearing 606 makes contact with proximal end 704 of second housing 700 when movable member 600 travels toward lancing device proximal end 108 of lancing device 100, and it makes contact with inner surface 706 of second housing 700 when it travels along the length of second housing 700 in either direction. Distal bearing 608 also makes contact with inner surface 706 of second housing 700 when it travels along the length of second housing 700 in either direction. The clearance between proximal bearing 606, distal bearing 608, and inner surface 706 is small (on the order of less than 0.1 inches), providing smooth, tight motion, as opposed to sloppy, loose motion. First bias member 104 is mounted inside launch spring housing 610, centered on launch spring pin 613 and resting upon launch spring support 612. First bias member 104 is free to expand and contract, and provides a motive force for moving movable member 600 back and forth along the axis between lancing device proximal end 108 and lancing device distal end 110. Plurality of arms 614 are connected to collet spring support 620 on one end, and to collet positioning tabs 616 on the other. Plurality of arms 614 increase in thickness as they reach collet-positioning tabs 616, and can grasp or not grasp lancet L as collet 500 moves along their length. This is illustrated in FIGS. 17A-17D. Third bias member 102 is placed around plurality of arms 614, contacting collet spring support 620 on one end and spring support 508 on the other. When assembled, third bias member 102 is compressed, providing a biasing force that pushes collet 500 onto collet positioning tabs 616. Upon lancet ejection, however, movable member 600 is moved toward lancing device distal end 110 while collet 500 is fixed, moving collet positioning tabs 616 away from collet 500 and loosening the grip on the lancet.

This feature is illustrated in FIGS. 17A-17D. Stop arm 622 includes stop tip 624 which interacts with features on lancet depth adjustment member 300, such as, for example, loading stop 316, to limit motion of movable member 600 along the axis running between lancing device proximal end 108 and lancing device distal end 110. Stop arm 622 and stop tip 624 also interact with features on second housing 700, such as, for example, stop window 718, to prevent rotation of movable member 600 about the axis running between lancing device proximal end 108 and lancing device distal end 110. In an embodiment of the invention, stop tip 624 is at least partially made with an acoustically dampened material, such as, for example, an elastomer, to minimize sound when firing lancing device 100. In other embodiments, features on lancet depth adjustment member 300, such as, for example, loading stop 316, can also include acoustically dampened materials, such as, for example, an elastomer. Firing arm 626 includes priming indicator 628 and priming catch 629. Priming indicator 628 can be viewed through firing button 806 when movable member 600 has moved to the primed position and is ready to fire. In some embodiments, movable member 600 (including priming indicator 628) is pigmented to enhance visibility through firing button 806. In other embodiments priming indicator 628 can include a region that is painted or printed a bright color. Priming catch 629 catches on features in second housing 700 when primed, and releases when pressed down by contact 802, as illustrated in FIG. 24. When priming catch 629 is released, movable member 600 is pushed forward towards lancing device distal end 110 by first bias member 104. While movable member 600 is traveling forward, return arm 630 grabs and extends second bias member 106, eventually pulling movable member 600 back to its rest position, towards the middle of second housing 700. Movable member 600 can be at least partially clear or opaque, and can be made using rigid materials. For example, movable member 600 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. In some embodiments lubricants are added to the thermoplastic, to minimize friction between movable member 600 and other parts, such as, for example, second housing 700. Conversely, lubricants can be added to the other parts, such as, for example, second housing 700, as long as the friction between movable member 600 and the other parts, such as, for example, second housing 700, remains small. Various lubricants can be used, such as, for example, fluoropolymers or silicones.

Figure 7:
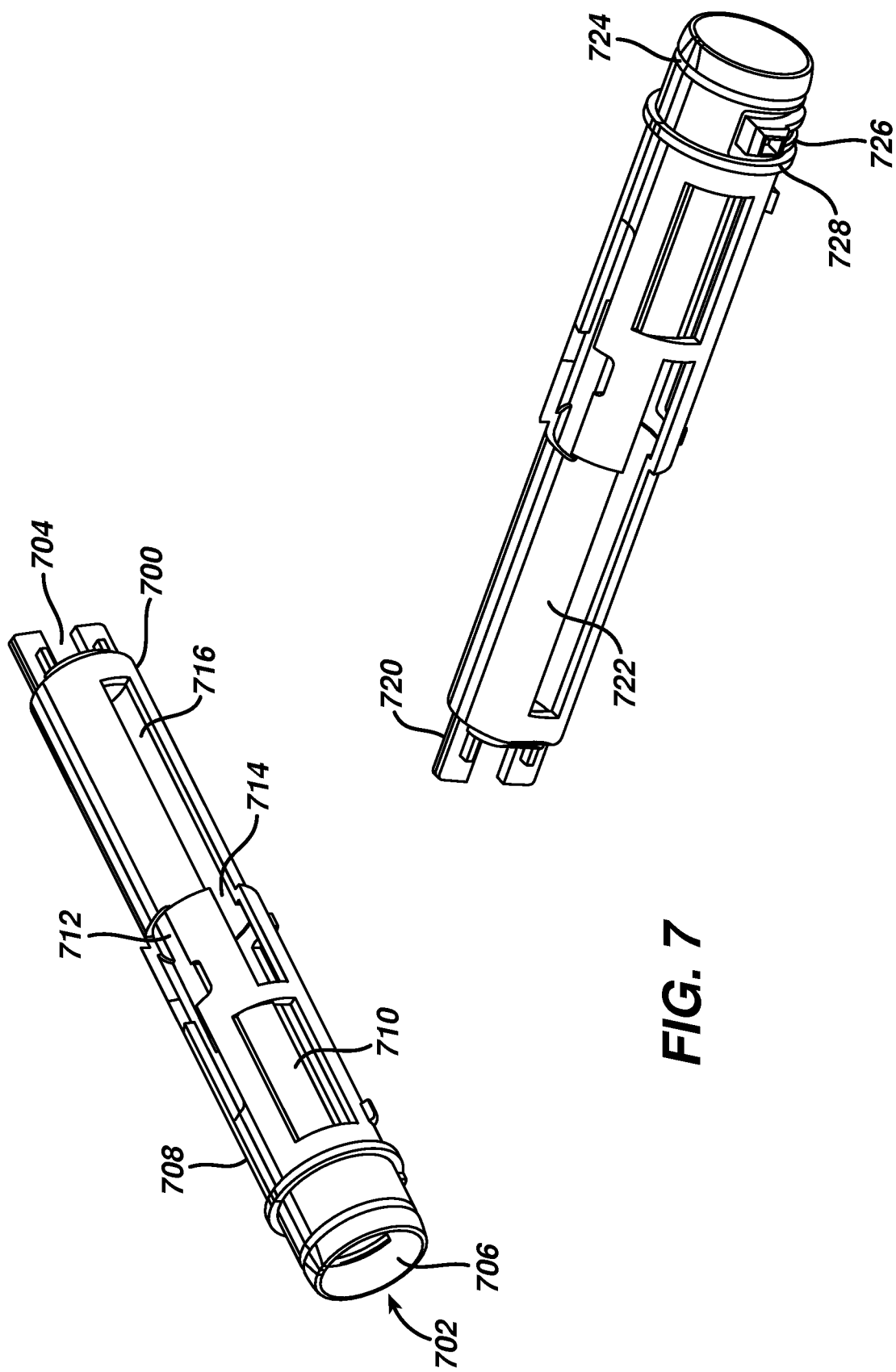
FIG. 7 illustrates two perspective views of a second housing, according to an embodiment described and illustrated herein.

FIG. 7 illustrates two perspective views of second housing 700, according to an embodiment described and illustrated herein. Second housing 700 includes distal end 702, proximal end 704, inner surface 706, outer surface 708, grip window 710, firing window 712, priming window 714, return window 716, stop window 718, positioning ribs 720, mandrel 722, positioning groove 724, depth detent 726, and positioning rib 728. Inner surface 706 and outer surface 708 extend from proximal end 704 to distal end 702, and provide smooth contact surfaces for mating parts, such as, for example, proximal bearing 606, distal bearing 608, first actuator 900, and third actuator 1000. Grip window 710, firing window 712, priming window 714, return window 716, and stop window 718 (stop window 718 is shown in FIG. 19E, not in FIG. 7) provide access between the inside and outside of second housing 700, and in some cases provide contact surfaces that register other parts to second housing 700. Positioning ribs 720 interact with features in first housing bottom 1100 and first housing top 1200, such as, for example, positioning ribs 1110 and positioning ribs 1206. Mandrel 722 provides inside support for second bias member 106, while return window 716 allows return arm 630 to grip second bias member 106. As mentioned previously, positioning groove 724 provides a guide for positioning ribs 404, while collar 400 rotates about the perimeter of second housing 700. Depth detent 726 engages chassis engaging ribs 308 when adjusting the penetration depth of lancet L using lancet depth adjustment member 300. In some embodiments, a click is felt as depth detent 726 engages chassis engaging ribs 308, providing tactile and/or audible feedback that lancet depth adjustment member 300 has been positioned correctly. Positioning rib 728 interacts with lancet depth adjustment member 300, providing a positioning guide and limit against which lancet depth adjustment member 300 rotates. Second housing 700 can be at least partially clear or opaque, and can be made using rigid materials. For example, second housing 700 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. In some embodiments lubricants are added to the thermoplastic, to minimize friction between second housing 700 and other parts, such as, for example, movable member 600. Conversely, lubricants can be added to the other parts, such as, for example, movable member 600, as long as the friction between second housing 700 and the other parts, such as, for example, movable member 600 remains small. Various lubricants can be used, such as, for example, fluoropolymers or silicones.

Figure 8:
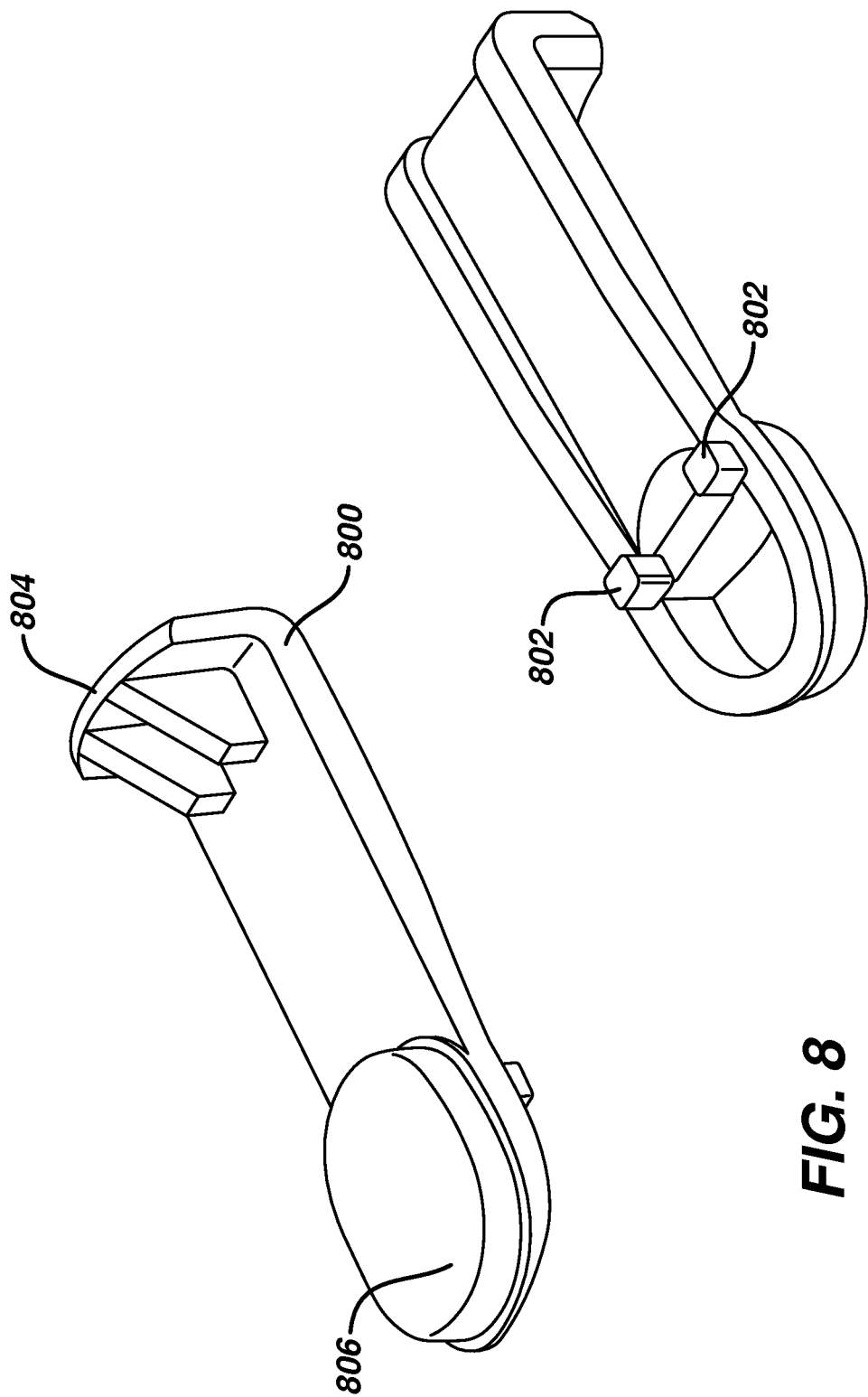
FIG. 8 illustrates two perspective views of a second actuator, according to an embodiment described and illustrated herein.

FIG. 8 illustrates two perspective views of second actuator 800, according to an embodiment described and illustrated herein. Second actuator 800 includes contact 802, positioning guide 804, and firing button 806. When lancing device 100 is fired, contact 802 makes contact with a feature on movable member 600, such as, for example, priming catch 629, releasing movable member 600 to travel towards lancing device distal end 110. Positioning guide 804 mates with features on first actuator 900, such as, for example, positioning pocket 906, allowing second actuator 800 and first actuator 900 to move as an assembly along the axis that runs between lancing device proximal end 108 and lancing device distal end 110. Firing button 806 passes through firing button window 902 and provides a distinct contact area for firing lancing device 100. Second actuator 800 can be at least partially clear or opaque, and can be made using rigid or flexible materials. For example, second actuator 800 can be injection molded using rigid thermoplastics, such as, for example, ABS, polycarbonate, acrylic, or polystyrene, or it can be injection or reaction injection molded using thermoplastic or thermosetting elastomers. In some embodiments, second actuator 800 is transparent, allowing visualization of features on movable member 600, such as, for example, priming indicator 628.

Figure 9:
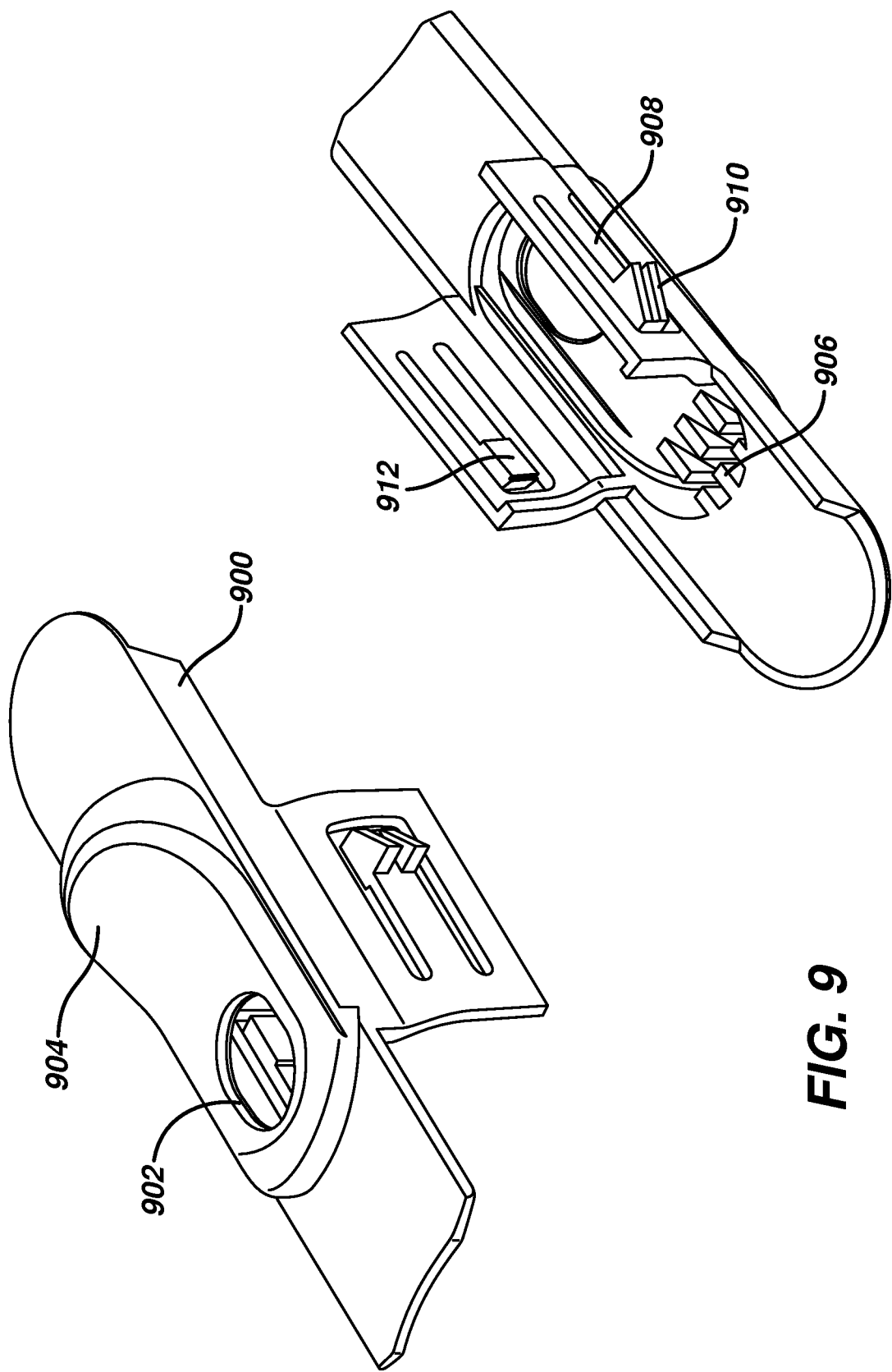
FIG. 9 illustrates two perspective views of a first actuator, according to an embodiment described and illustrated herein.

FIG. 9 illustrates two perspective views of first actuator 900, according to an embodiment described and illustrated herein. First actuator 900 includes firing button window 902, grip 904, positioning pocket 906, gripping arm 908, priming slide 910, and priming grip 912. As mentioned previously, firing button window 902 allows access to features on second actuator 800, such as, for example, firing button 806. In some embodiments, firing button 806 is transparent, and when first actuator 900 is moved back and forth (priming lancing device 100) priming indicator 628 appears through firing button 806. Lancing device 100 can then be fired by pressing firing button

806. This sequence is illustrated in FIGS. 19A-G. Grip 904 provides a contact surface, allowing the user to push first actuator 900 towards lancing device proximal end 108. Positioning pocket 906 grip features on second actuator 800, such as, for example, positioning guide 804, allowing second actuator 800 and first actuator 900 to move as an assembly. Gripping arm 908 is connected to priming slide 910 and priming grip 912, which allow first actuator 900 to grip and move movable member 600 during the priming step. As first actuator 900 moves towards lancing device proximal end 108, priming slide 910 contacts priming ramps 1302, pushing priming grip 912 inward and into contact with movable member 600. Priming grip 912 grips movable member 600, moving it towards lancing device proximal end 108. First actuator 900 can be at least partially clear or opaque, and can be made using rigid materials. For example, first actuator 900 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof.

FIG. 10 illustrates two perspective views of third actuator 1000, according to an embodiment described and illustrated herein. Third actuator 1000 includes eject button 1002, key 1004, flexible wall 1006, ejection slide 1008, and grip 1010. Eject button 1002 is moved towards lancing device distal end 110 when ejecting a lance from lancing device 100. Key 1004 mates with a feature on lancet depth adjustment member 300, such as, for example, groove 310, allowing movable member 600 to travel further towards lancing device distal end 110 and loosening the grip of plurality of arms 614 on lancet L. Flexible wall 1006 is connected to ejection slide 1008 on the outside, and to grip 1010 on the inside. When lancing device 100 is moved towards lancing device distal end 110, ejection slide 1008 contacts features on first housing bottom 1100, such as, for example, eject ramp 1104, causing flexible wall 1006 to flex inward and pushing grip 1010 through an opening in second housing 700 and against movable member 600. Grip 1010 grips movable member 600, allowing movable member 600 to move toward lancing device distal end 110 as third actuator 1000 is moved toward lancing device distal end 110. As third actuator 1000 returns to its rest position, grip 1010 disengages movable member 600, allowing movable member 600 to then move independently. Third actuator 1000 can be at least partially clear or opaque, and can be made using rigid materials. For example, first actuator 900 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof.

Figure 11:
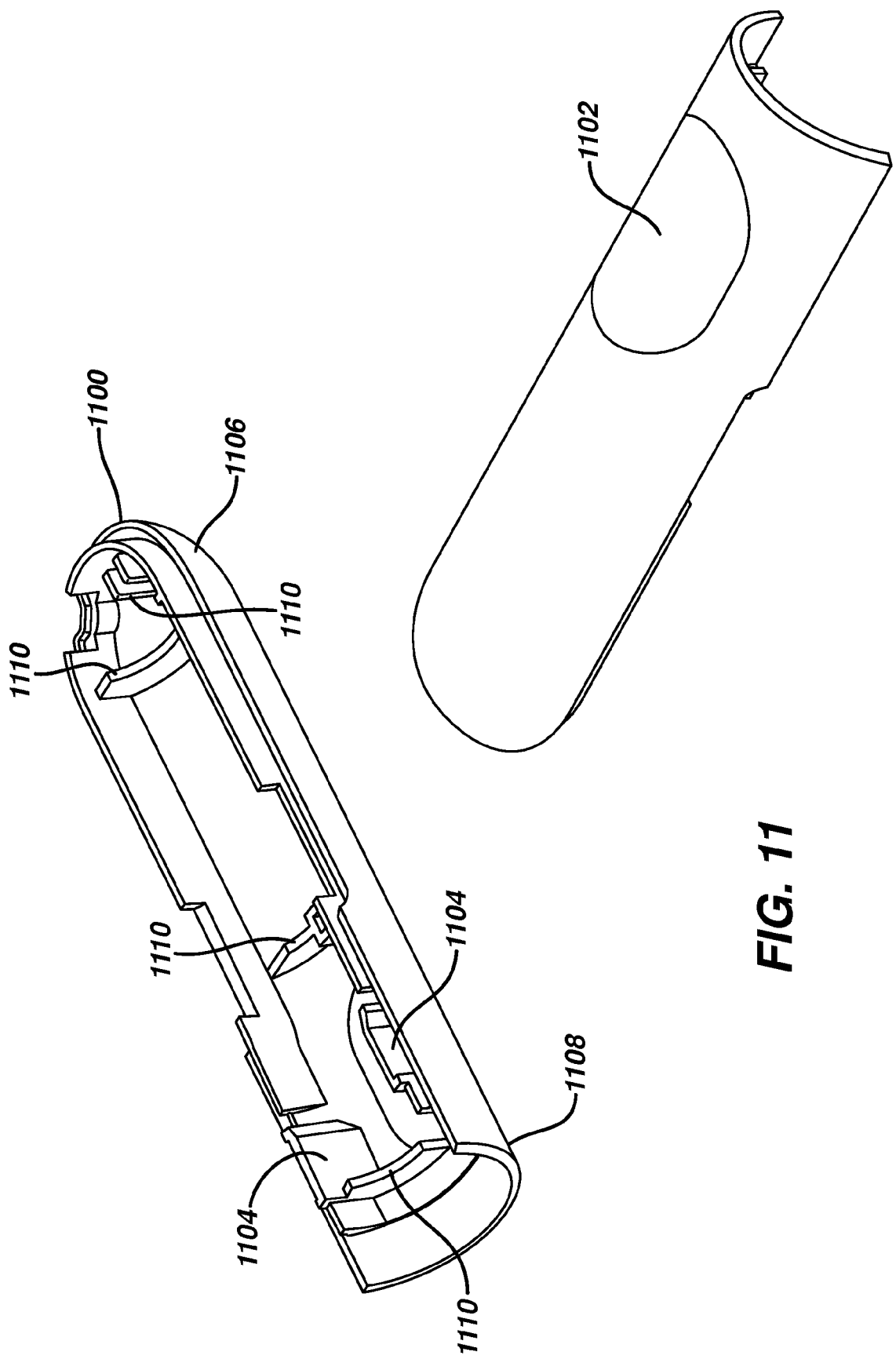
FIG. 11 illustrates two perspective views of a first housing bottom half, according to an embodiment described and illustrated herein.

FIG. 11 illustrates two perspective views of first housing bottom 1100, according to an embodiment described and illustrated herein. First housing bottom 1100 includes grip 1102, eject ramp 1104, distal end 1106, proximal end 1108, and positioning ribs 1110. Grip 1102 allows for enhanced handling of lancing device 100, and in the embodiment illustrated in FIG. 11 is made by molding a recess in the outer surface of first housing bottom 1100. Other embodiments could include the use of additional materials, such as, for example, over-molded elastomers. Eject ramp 1104 interacts with features on third actuator 1000, such as, for example, ejection slide 1008, to impart motion in parts of third actuator 1000 that are perpendicular to the axis running between lancing device proximal end 108 and lancing device distal end 110. Positioning ribs 1110 are located at various points along the inner surface of first housing bottom 1100, and interact with the outer surface of second housing 700, positioning second housing 700 in a stationary and precise location within first housing bottom 1100. First housing bottom 1100 can be at least partially clear or opaque, and can be made using rigid materials. For example, first housing bottom 1100 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. First housing bottom 1100 can also be formed of semi-rigid materials including, for example, polypropylene, high-density polyethylene, polyurethane, ethylene propylene rubber, polymethylpentene and combinations thereof.

Figure 12:
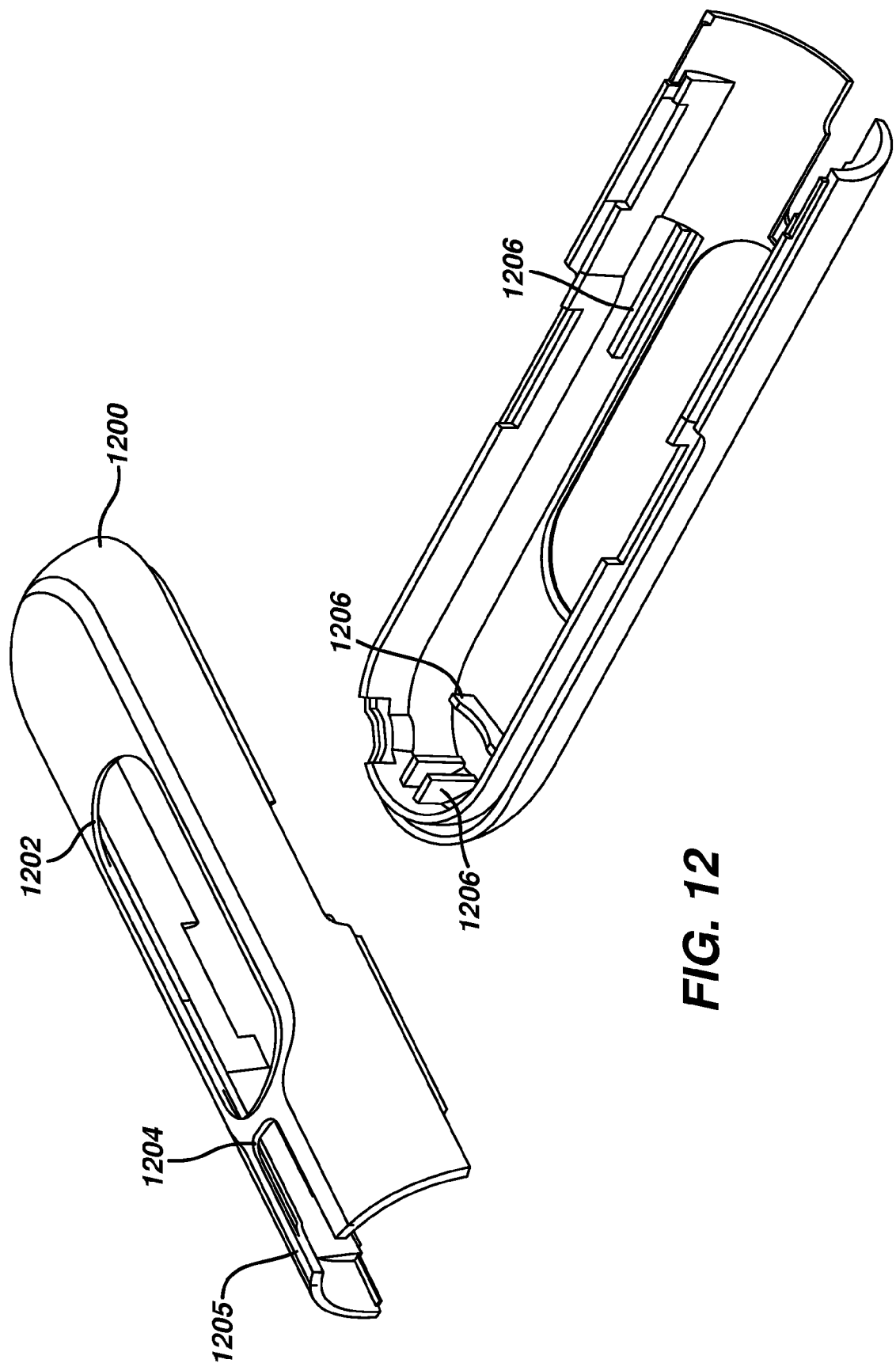
FIG. 12 illustrates two perspective views of a first housing top half, according to an embodiment described and illustrated herein.

FIG. 12 illustrates two perspective views of first housing top 1200, according to an embodiment described and illustrated herein. First housing top 1200 includes priming window 1202, ejection window 1204, depth window 1205, and positioning ribs 1206. Priming window 1202 allows access to features on first actuator 900, such as, for example, grip 904, and to features on second actuator 800, such as, for example, firing button 806. Priming window 1202 is sized such that it allows grip 904 to travel from its rest position to its prime position, and back. Ejection window 1204 allows access to features on third actuator 1000, such as, for example, eject button 1002, and is sized to allow eject button 1002 to travel from its rest position to its eject position, and back. Depth window 1205 allows features on lancet depth adjustment member 300 to be visualized, such as, for example, depth indicator 302. Depth window 1205 is sized to allow a single element of depth indicator 302 to be visualized at a time. Positioning ribs 1206 are located at various points along the inner surface of first housing top 1200, and interact with the outer surface of second housing 700, positioning second housing 700 in a stationary and precise location within first housing top 1200. First housing top 1200 can be at least partially clear or opaque, and can be made using rigid materials. For example, first housing top 1200 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. First housing top 1200 can also be formed of semi-rigid materials including, for example, polypropylene, high-density polyethylene, polyurethane, ethylene propylene rubber, polymethylpentene and combinations thereof.

Figure 13:
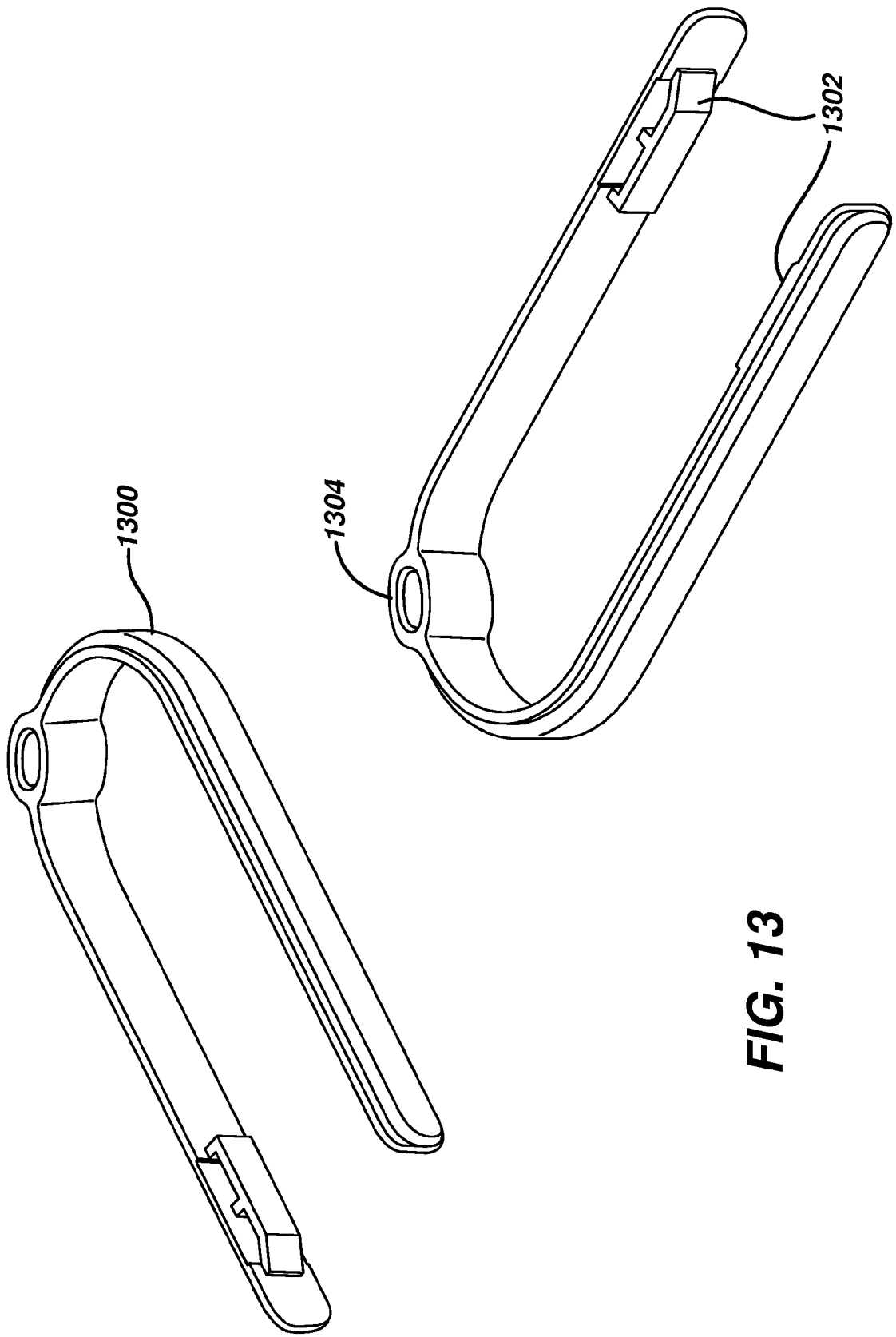
FIG. 13 illustrates two perspective views of a band, according to an embodiment described and illustrated herein.

FIG. 13 illustrates two perspective views of band 1300, according to an embodiment described and illustrated herein. Band 1300 includes priming ramps 1302 and eyelet 1304. Priming ramps 1302 interacts with features on first actuator 900, such as, for example, priming slide 910, when first actuator 900 is moved toward lancing device proximal end 108 when priming lancing device 100. As 910 moves along priming ramps 1302, gripping arm 908 moves inward, pushing priming grip 912 through an opening in second housing 700 and into contact with movable member 600. Priming grip 912 grips movable member 600, moving it towards lancing device proximal end 108 as first actuator 900 moves towards lancing device proximal end 108. Eyelet 1304 provides a fastening point for key rings or other optional accessories. Band 1300 can be at least partially clear or opaque, and can be made using rigid materials. For example, band 1300 can be injection molded using rigid thermoplastics, including, but not limited to, ABS, acrylic, polycarbonate, polyester, polystyrene, polyamide, polyacetal, polyimide, polyketone, polyurethane, polybutyleneteraphthalate and combinations thereof. Band 1300 can also be formed of semi-rigid materials including, for example, polypropylene, high-density polyethylene, polyurethane, ethylene propylene rubber, polymethylpentene and combinations thereof.

Having described various components of lancing device 100, details of the interaction and functioning of such components will now be described with reference to FIGS. 14 through 19.

FIGS. 14A-14D illustrate a sequence of steps used in setting an eject position and opening the cap of lancing device 100, according to an embodiment described and illustrated herein.

Figure 14A:
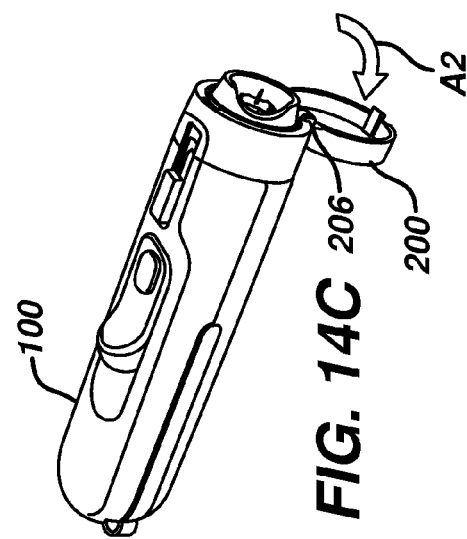
FIGS. 14A-14D illustrate a sequence of steps used in setting an eject position and opening the cap of a lancing device, according to an embodiment described and illustrated herein.
Figure 14B:
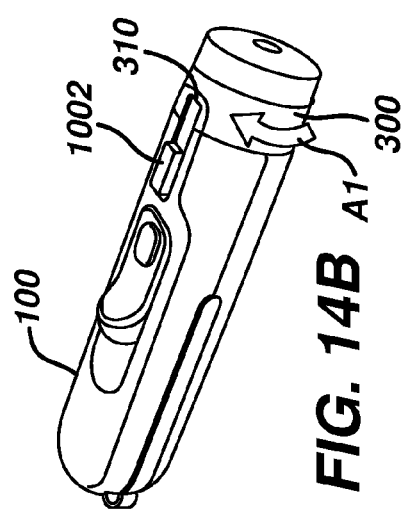
Figure 14C:
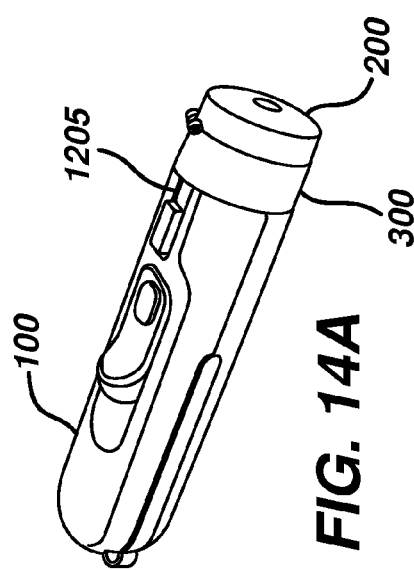
Figure 14D:
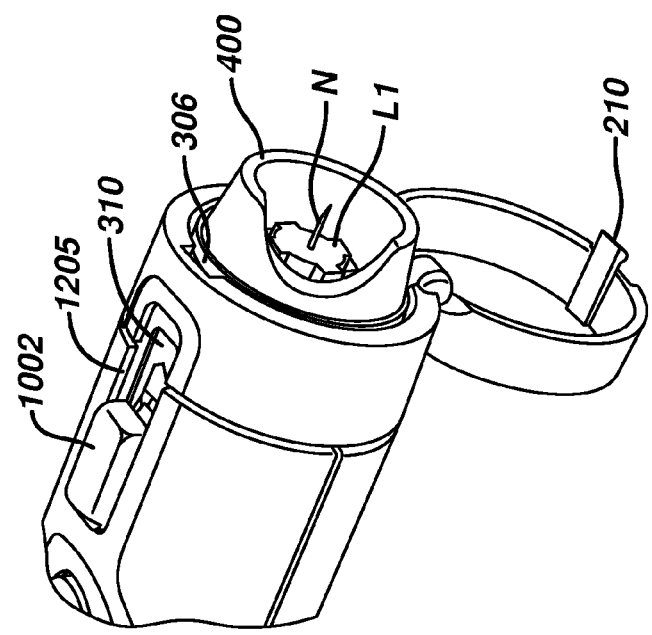

In FIG. 14A, lancing device 100 is at rest. In this state, lancing device 100 is not primed, has already been fired, and contains lancet L1. Lancet depth adjustment member 300 is set to 5, and can be seen through depth window 1205. Cap 200 is closed. In FIG. 14B, lancet depth adjustment member 300 is rotated to the eject position, as indicated by arrow A1. Groove 310 lines up with eject button 1002, allowing key 1004 (not shown) to enter groove 310 during the subsequent eject step (illustrated in FIGS. 15C-15D). In FIGS. 14C and 14D, cap 200 is opened, as indicated by arrow A2. In opening cap 200, latch 210 unclips from clasp 306, and pivots about hinge 206. Once cap 200 is opened, collar 400 and lancet L1 are exposed. Lancet L1 is partially covered by collar 400, preventing inadvertent puncture by needle N. By rotating lancet depth adjustment member 300 into the eject position, as illustrated in FIGS. 14B-14D, eject button 1002 can be advanced into groove 310, extending lancet L1 beyond collar 400 (as seen in FIG. 15D).

Figure 15E:
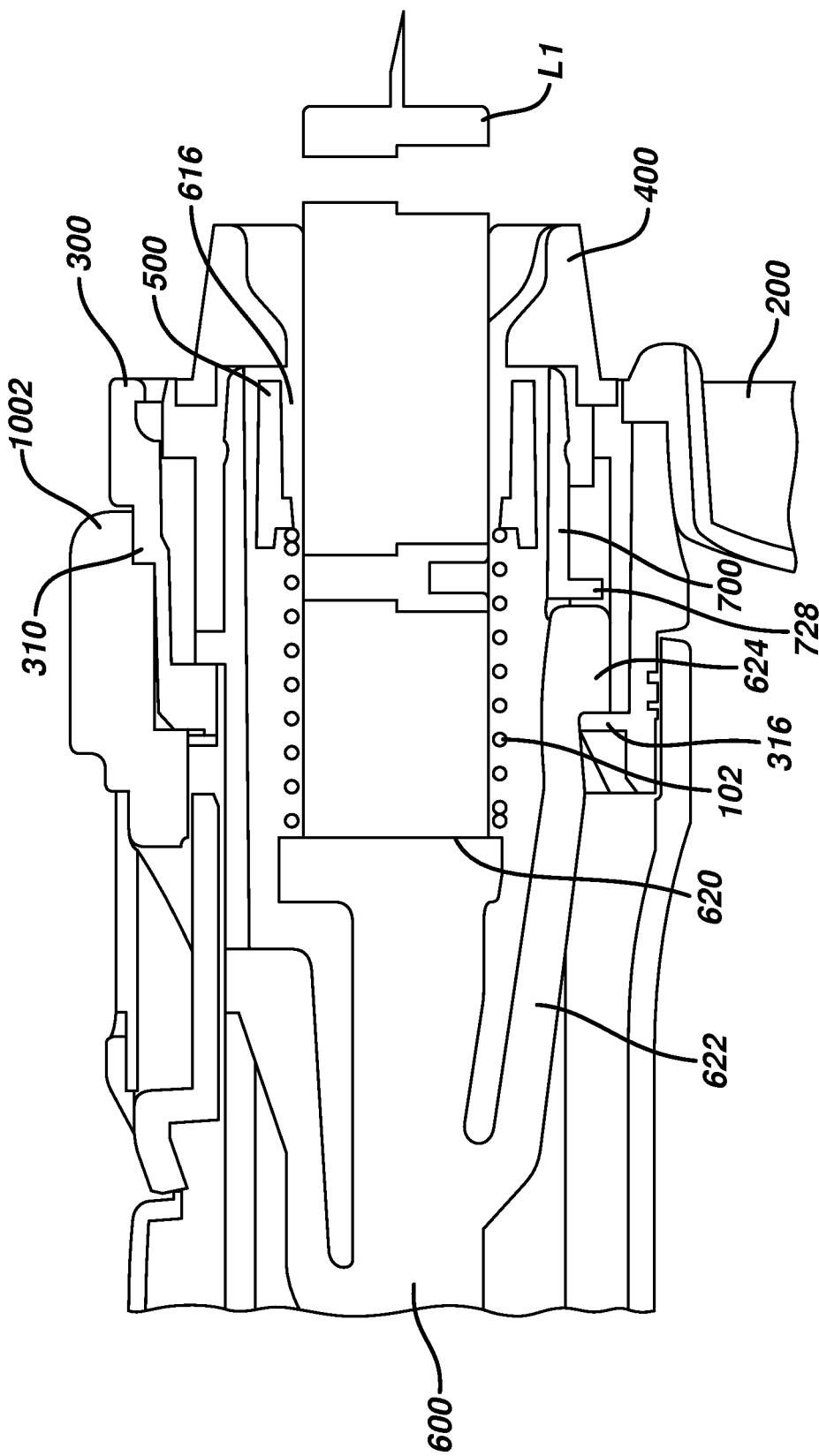

FIGS. 15A-15E illustrate a sequence of steps used in capping a lancet in lancing device 100, according to an embodiment described and illustrated herein. In FIG. 15A, lancing device 100 is in the stage illustrated in FIGS. 14C and 14D. Lancet depth adjustment member 300 is in the eject position, eject button 1002 has not been moved forward, and cap 200 is open, exposing lancet L1. To cap lancet L1, lancet cover C2 is inserted into collar 400 and onto lancet L1, as indicated by arrow A3. In FIG. 15B, lancet cover C2 is pushed completely onto lancet L1, as indicated by arrow A4. Since unused-lancet L2 is a new lancet, it is still connected to lancet cover C2. In FIGS. 15C and 15D, eject button 1002 is moved forward, as indicated by arrow A5, moving movable member 600 forward relative to collet 500, loosening the grip of collet positioning tabs 616 on lancet L1. FIG. 15D is a cross sectional detail of the lancing device distal end 110 portion of lancing device 100 during the stage illustrated by FIG. 15C. FIG. 15E is the same cross sectional detail shown in FIG. 15D, shown in larger scale. Once collet positioning tabs 616 loosens its grip on lancet L1, lancet L1, lancet cover C2, and unused-lancet L2 can be removed from lancing device 100, as illustrated in FIG. 15C. In FIGS. 15D and 15E, eject button 1002 has been pushed forward and stops against groove 310. Lancet depth adjustment member 300 has been positioned so that groove 310 is aligned with eject button 1002. Collar 400 is fixed to second housing 700, while collet positioning tabs 616 has moved forward relative to collet 500, loosening its grip upon lancet L1. Third bias member 102 is compressed, and sits against collet spring support 620. Stop tip 624 is connected to stop arm 622, and has been pushed over loading stop 316 next to positioning rib 728, locking movable member 600 in place.

Figure 16E:
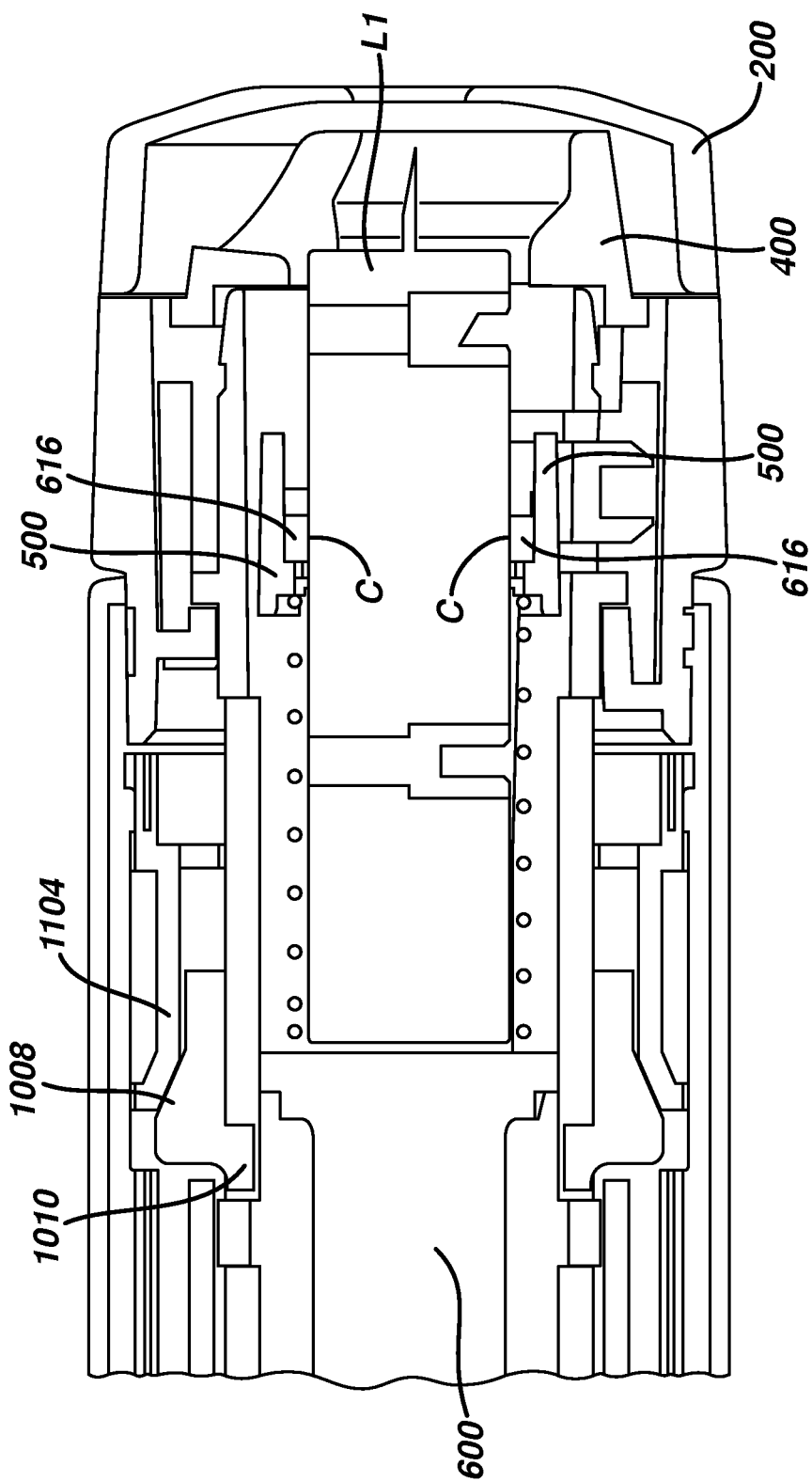
Figure 16F:
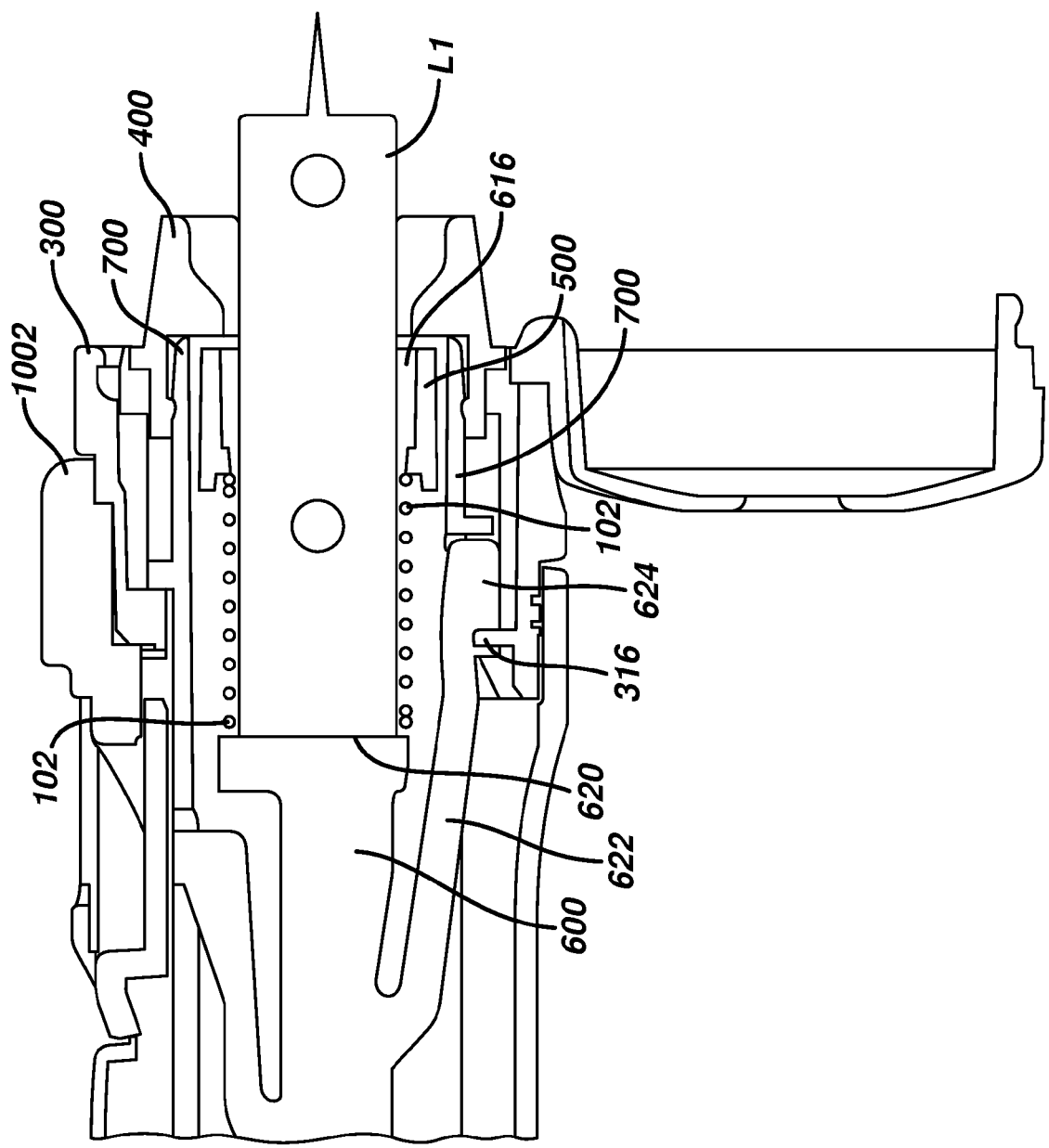

In FIGS. 16A-16F, collet-positioning tabs 616 sit in positioning pockets 504, forcing plurality of arms 614 against lancet L1, and securely holding lancet L1 in movable member 600. Third bias member 102 presses against collet 500, forcing it against collet positioning tabs 616 and maintaining a retaining grip on lancet L1. Referring now to FIG. 16C, as eject button 1002 is moved in the direction indicated by arrow A9, ejection slide 1008 moves against eject ramp 1104, causing grip 1010 to move in the direction indicated by arrow A8, grasping movable member 600. As eject button 1002 continues to move in the direction indicated by arrow A9, movable member 600 moves in the direction indicated by arrow A7 and arrow A10. As movable member 600 moves in the direction indicated by arrow A10, stop arm 622 flexes and stop tip 624 rides over and catches on loading stop 316, holding movable member 600 firmly in place. As movable member 600 moves in the direction indicated by arrow A10, collet-positioning tabs 616 disengages from positioning pockets 504, releasing the grip between plurality of arms 614 and lancet L1. Once the grip between plurality of arms 614 and lancet L1 has been released, lancet L1 can be removed directly by hand, or can be removed using the procedure illustrated in FIGS. 17A-17D.

Figure 17A:
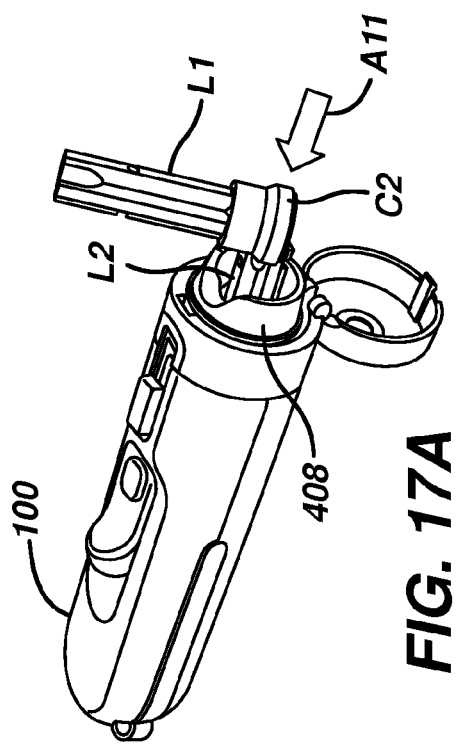
FIGS. 17A-17D illustrate a sequence of steps used in loading a lancet into a lancing device and setting its penetration depth, according to an embodiment described and illustrated herein.
Figure 17B:
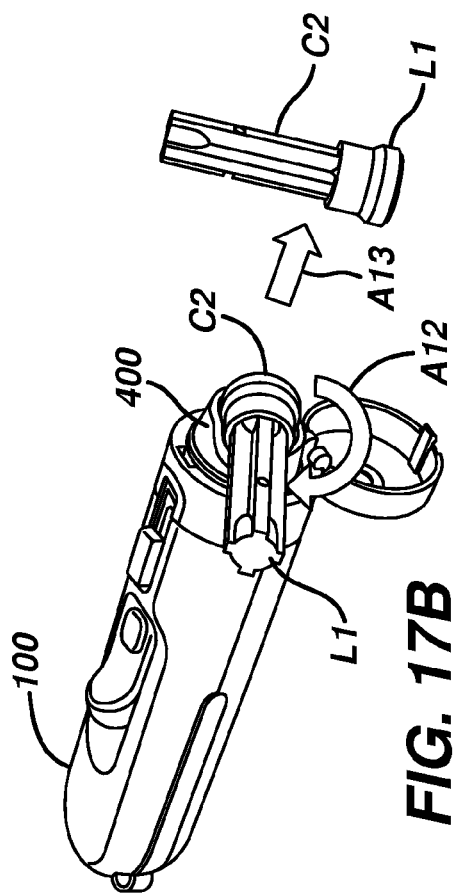
Figure 17C:
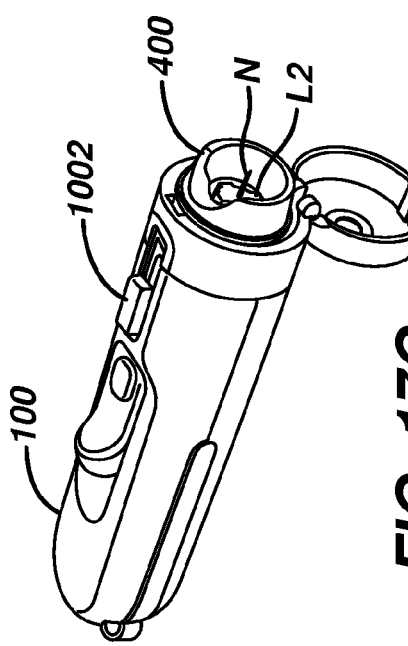
Figure 17D:
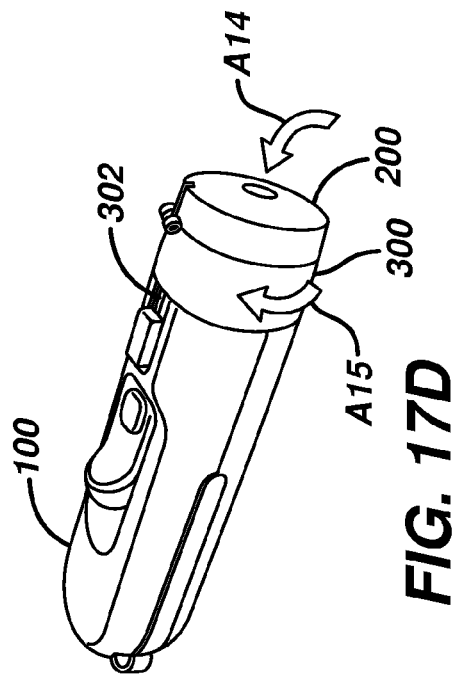

FIGS. 17A-17D illustrate a sequence of steps used in loading a lancet into a lancing device and setting its penetration depth, according to an embodiment described and illustrated herein. In the step illustrated in FIG. 17A, unused-lancet L2 is inserted into movable member 600, and pressed firmly until it stops, as indicated by arrow A11. In some embodiments, unused-lancet L2 is attached to lancet cover C2 and lancet L1, as previously described in reference to FIG. 15C. If lancet cover C2 and lancet L1 are attached to unused-lancet L2, lancet L1 can be used as a lever, to rotate lancet cover C2 and break it free from unused-lancet L2, as illustrated in FIG. 17B. Once lancet L1 and lancet cover C2 are free from unused-lancet L2, they can be disposed of appropriately. Lancet cover C2 covers needle N, helping to prevent inadvertent needle sticks. While lancet L1 is rotated, collar 400 rotates as well, keeping cutaway 408 aligned with lancet L1. In FIG. 17C, eject button 1002 has returned to its at rest position, pulling unused-lancet L2 back into lancing device 100, and protecting needle N within collar 400. In step 17D, cap 200 is closed, as indicated by arrow A14, and penetration depth is set using lancet depth adjustment member 300, as indicated by arrow A15. Lancing device 100 is now ready to be primed, as illustrated in FIGS. 18A-18E.

Figure 18D:
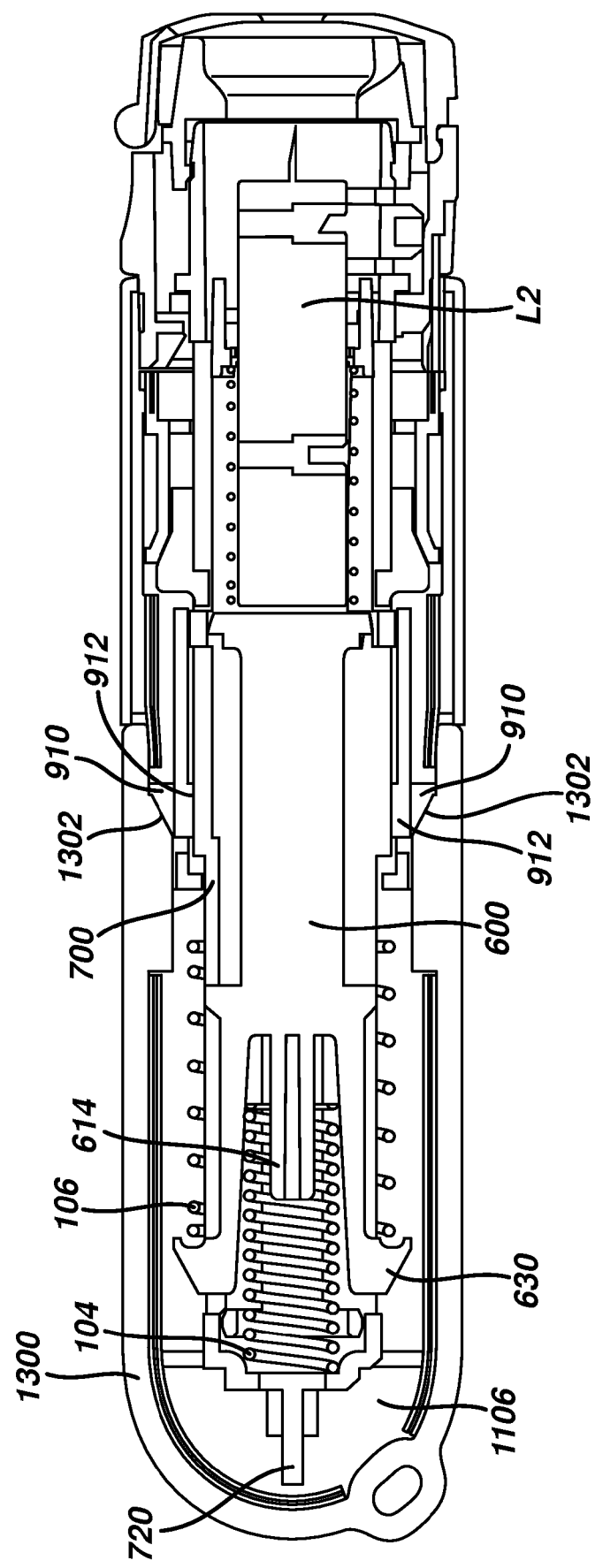
Figure 18E:
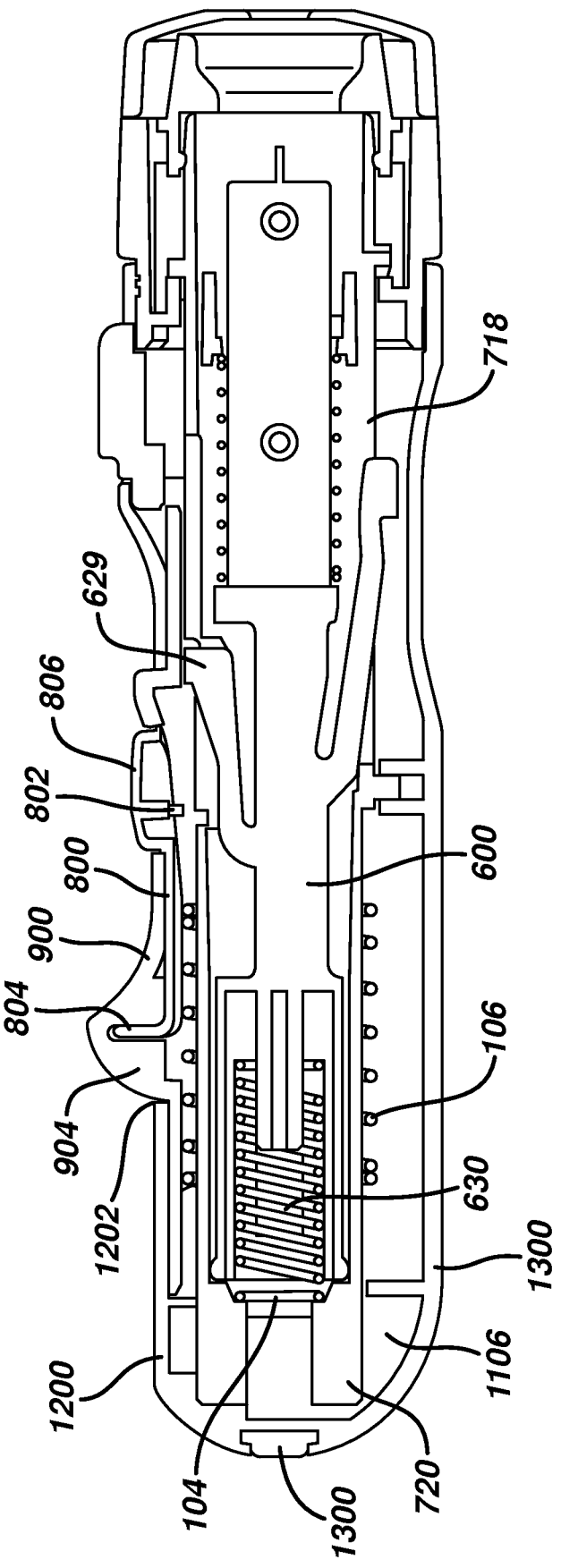

FIGS. 18A-18E illustrate a sequence of steps used in priming a lancing device, according to an embodiment described and illustrated herein. FIG. 18A is a perspective view of lancing device 100 while being primed, FIG. 18B is a top plan cross sectional view at the beginning of the priming sequence, FIG. 18C is a side cross sectional view when movable member 600 has been primed, FIG. 18D is an enlarged view of FIG. 18B, and FIG. 18E is an enlarged view of FIG. 18C. In FIGS. 18A, 18C, and 18E, grip 904 has been moved back, as indicated by arrow A16. In reference to FIGS. 18B and 18D, as grip 904 moves back, priming slide 910 encounters priming ramps 1302, moving priming grip 912 in the direction indicated by arrow A18 and through an opening in second housing 700. Eventually, priming grip 912 makes contact with movable member 600, griping and moving it in the direction of arrow A17 as grip 904 moves in the direction indicated by arrow A16. When grip 904 reaches the edge of priming window 1202, priming catch 629 catches on an edge of firing window 712, keeping movable member 600 in a proximal and primed position, as illustrated in FIGS. 18C and 18E. The user then lets go of grip 904, returning second actuator 800 and first actuator 900 to their original at rest position toward the distal end of priming window 1202. Second bias member 106 provides the motive force for moving second actuator 800 and first actuator 900 toward the distal end of priming window 1202. When movable member 600 is in the primed position, first bias member 104 is compressed. When released, first bias member 104 provides the motive force that propels movable member 600 and unused-lancet L2 forward into a lancing position.

Figure 19C:
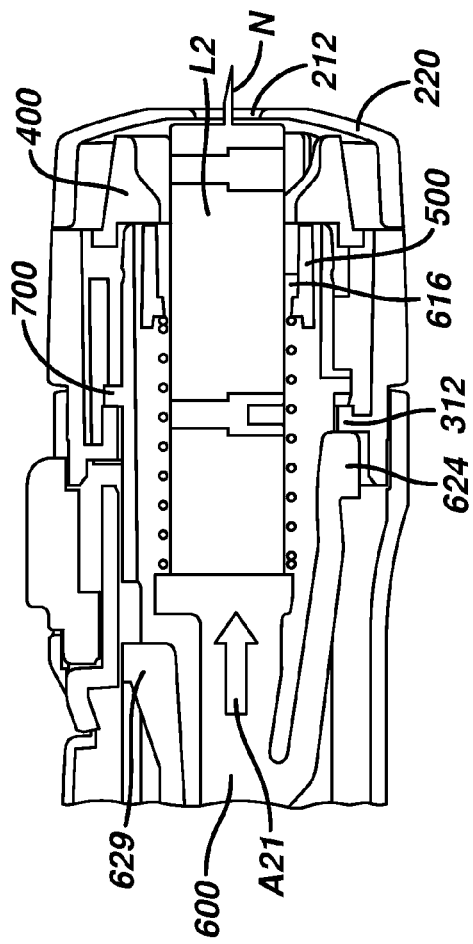
FIGS. 19A-19G illustrate a sequence of steps used in firing a lancing device, according to an embodiment described and illustrated herein.
Figure 19D:
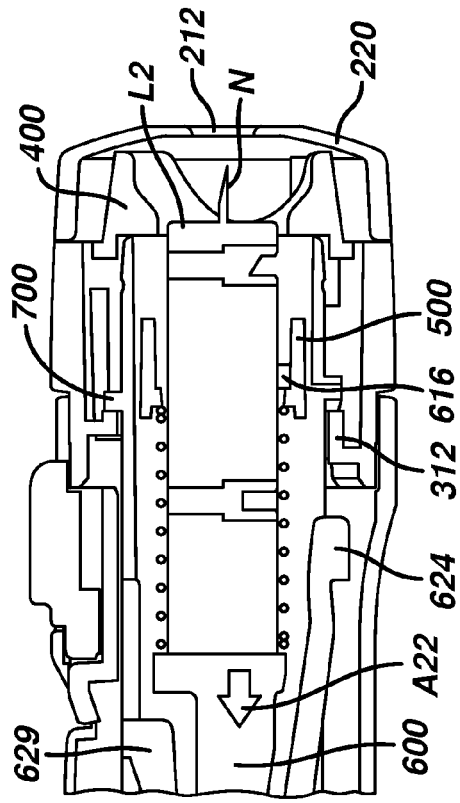
Figure 19A:
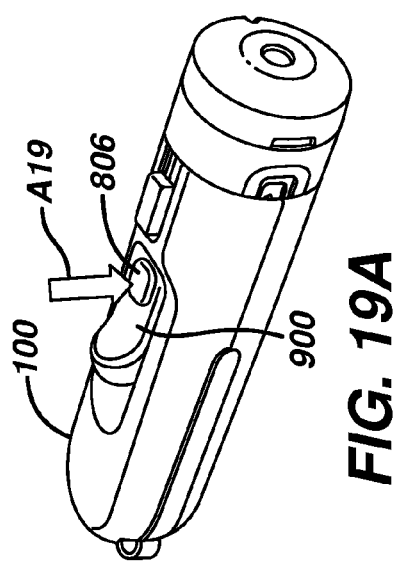
Figure 19B:
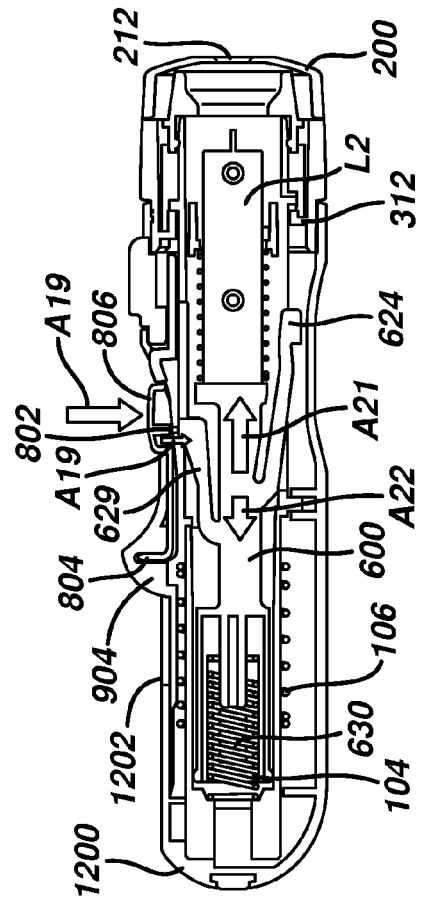
Figure 19E:
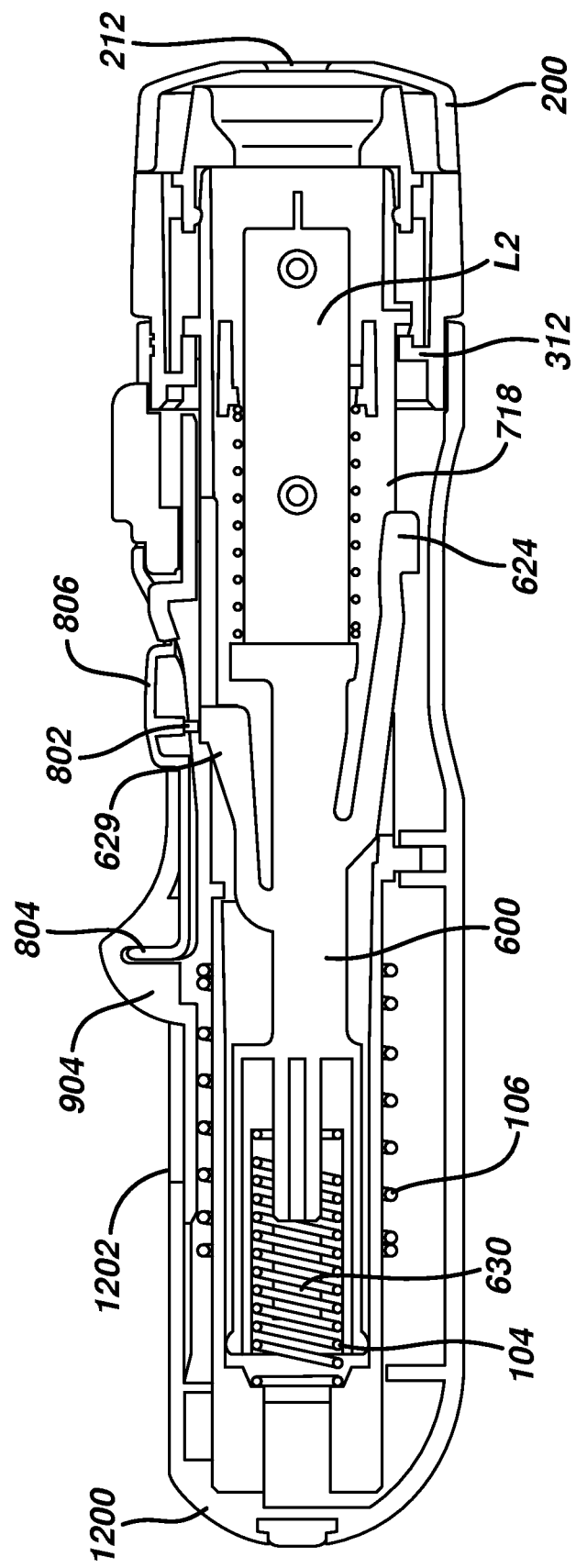
Figure 19F:
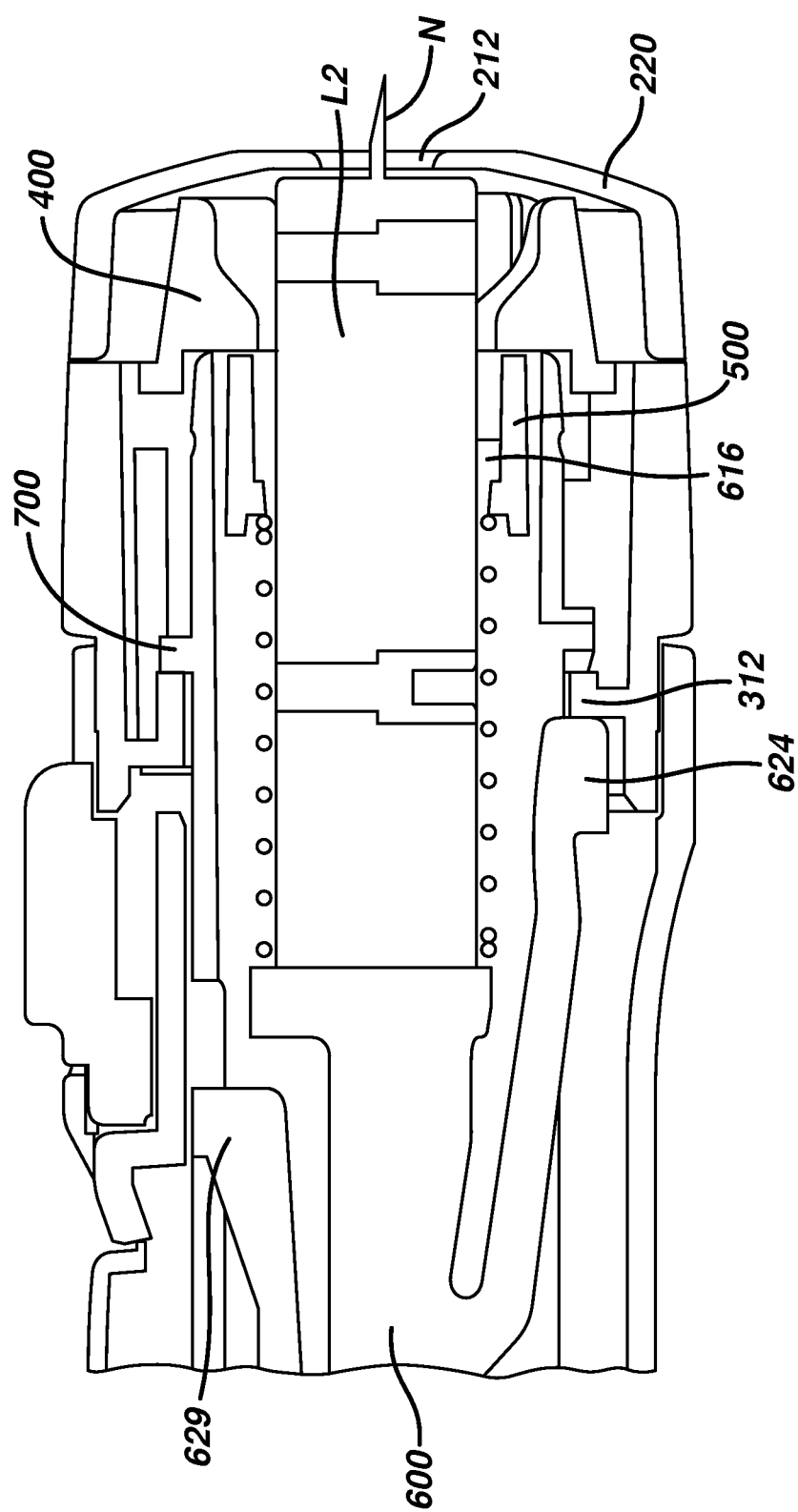
Figure 19G:
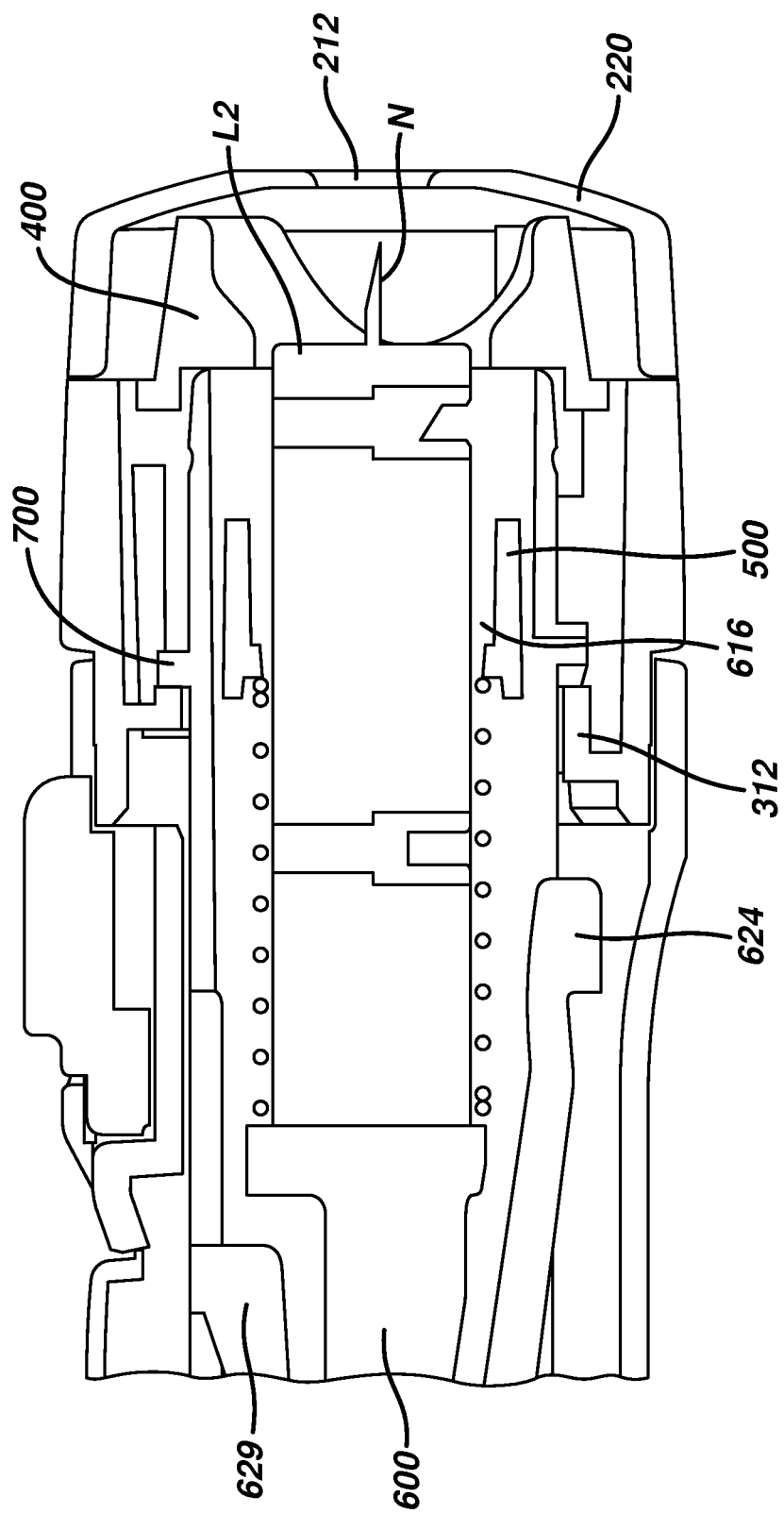

FIGS. 19A-19G illustrate a sequence of steps used in firing a lancing device, according to an embodiment described and illustrated herein. FIG. 19A is a perspective view of lancing device 100 at the time of firing, FIG. 19B is a side cross sectional view at the beginning of the firing sequence, FIG. 19C is a side cross sectional view of the distal end of lancing device 100 when movable member 600 has been fired and unused-lancet L2 is at its maximum lancing position, FIG. 19D is a side cross sectional view of the distal end of lancing device 100 when movable member 600 and unused-lancet L2 have returned to their at rest home position at the end of the firing sequence, FIG. 19E is an enlarged view of FIG. 19B, FIG. 19F is an enlarged view of FIG. 19C, and FIG. 19G is an enlarged view of FIG. 19D. In FIGS. 19A, 19B, and 19E, the firing sequence is initiated by pressing firing button 806, as indicated by arrow A19. As firing button 806 is pressed, contact 802 travels down, as indicated by arrow A19, and makes contact with priming catch 629. As priming catch 629 is pushed down, it breaks free of firing window 712, allowing first bias member 104 to push movable member 600 in the direction indicated by arrow A21. Eventually, stop tip 624 strikes depth stop 312, limiting its forward penetration, as illustrated in FIGS. 19C and 19F. As mentioned earlier, stop tip 624 and/or depth stop 312 can include an elastomer or other materials that dampen the sound when stop tip 624 strikes depth stop 312. As stop tip 624 strikes depth stop 312, unused-lancet L2 reaches its maximum travel, allowing needle N to pass through opening 212 and penetrate its target area, such as a users skin. After unused-lancet L2 has reached its maximum travel, second bias member 106 pulls movable member 600 back, eventually positioning movable member 600 at its home position, as illustrated in FIGS. 19D and 19G. At this point, the sequences illustrated in FIGS. 14-19 can be repeated.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A lancing device comprising:
a first housing having spaced apart proximal and distal ends disposed along a longitudinal axis;
a second housing disposed in the first housing and fixedly to the first housing;
a movable member disposed in the second housing and configured for movement along the longitudinal axis and in the first housing wherein the moveable member includes a plurality of arms extending away from the longitudinal axis towards the distal end;
a lancet coupled to the movable member;
a lancet depth adjustment member captured by both the first and second housings so that the lancet depth adjustment member is rotatable relative to both housings to provide for a plurality of stop surfaces to the movable member:
a first bias member located in the second housing to bias the moveable member in a direction towards the distal end;
a first actuator coupled to the moveable member so that the movable member is positioned proximate the proximal end in a primed-position;
a second actuator carried on a portion of the first actuator, the second actuator configured to allow the movable member to move from the primed-position proximate the distal end; and
a collect mounted on the plurality of arms for movement of the collect along the longitudinal axis on the plurality of arms from a first position of the collect in which the plurality of arms constrains the body of the lancet from movement and a second position of the collet in which the body of the lancet is free to move without constraint by the plurality of arms.

2. The lancing device of claim 1, further comprising:
a lancet ejection mechanism including:
a third actuator mounted to the first housing, the third actuator being disposed in:
a first position in which the third actuator is disengaged from both the lancet depth adjustment member and the moveable member, and
a second position in which the third actuator is connected to the moveable member with the depth adjustment member in a specific position so that a portion of the third actuator is displaced partially in a groove formed on a circumferential portion of the depth adjustment member to move the moveable member towards the distal end to eject the lancet.

3. The lancing device of claim 2, further comprising:
a collar disposed between the depth adjustment member and the collet, the collar configured to prevent movement of the collet towards the distal end.

4. The lancing device of claim 3, further comprising a cap to cover an aperture in which the lancet can extend from the depth adjustment member, the cap being connected to the depth adjustment member.

5. The lancing device of claim 2, further comprising a third bias member coupled to the moveable member to bias the collet in a direction towards the distal end.

6. The lancing device of claim 2, in which the first bias member comprises a resilient member in contact with the moveable member.

7. The lancing device of claim 1, in which the first housing comprises two halves connected together.

8. The lancing device of claim 1, in which the second housing comprises a unitary member connected to a positioning band coupled to the first housing, the second housing having at least one groove that extends through the unitary member along the longitudinal axis to allow communication from the inside of the second housing to the inside of the first housing.

9. The lancing device of claim 8, in which the moveable member comprises at least one return arm that extends through the groove so that the moveable member is guided by the at least one return arm along a path defined by the at least one groove.

10. The lancing device of claim 1, further comprising a second bias member configured to bias the moveable member in a direction towards the proximal end.

11. The lancing device of claim 10, in which the second bias member comprises a helical spring disposed outside the second housing and connected to the at least one return arm.

12. The lancing device of claim 10, in which the second bias member is selected from a group consisting of springs, magnets, or combinations thereof.

13. A lancing device comprising:
a first housing having spaced apart proximal and distal ends disposed along a longitudinal axis;
a second housing disposed in the first housing and fixedly attached to the first housing;
a movable member disposed in the second housing and configured for movement along the longitudinal axis and in the first housings wherein the moveable member includes a plurality of arms extending away from the longitudinal axis towards the distal end;
a bias member located in the second housing to bias the moveable member in a direction towards the distal end;
a first actuator coupled to the movable member so that the movable member is positioned proximate the proximal end in a primed-position;
a second actuator carried on a portion of the first actuator, the second actuator configured to allow the movable member to move from the primed-position to a position proximate the distal end; and
a lancet coupled to the movable member; and
a collet mounted on the plurality of arms for movement of the collet along the longitudinal axis on the plurality of arms from a first position of the collet in which the plurality of arms constrains the body of the lancet from movement and a second position of the collet in which the body of the lancet is free to move without constraint by the plurality of arms.

14. The lancing device of claim 13, further comprising:
a lancet ejection mechanism including:
a third actuator mounted to the first housing, the third actuator being disposed in:
a first position in which the third actuator is disengaged from both the lancet depth adjustment member and the moveable member, and
a second position in which the third actuator is connected to the moveable member with the depth adjustment member in a specific position so that a portion of the third actuator is displaced partially in a groove formed on a circumferential portion of the depth adjustment member to move the moveable member towards the distal end to eject the lancet.

15. The lancing device of claim 14, further comprising:
a collar disposed between the depth adjustment member and the collet, the collar configured to prevent movement of the collet towards the distal end.

16. The lancing device of claim 15, further comprising a cap to cover an aperture in which the lancet can extend from the depth adjustment member, the cap being connected to the depth adjustment member.

17. The lancing device of claim 14, further comprising a third bias member coupled to the moveable member to bias the collet in a direction towards the distal end.

18. The lancing device of claim 14, in which the first bias member comprises a resilient member in contact with the moveable member.

19. The lancing device of claim 13, in which the first housing comprises two halves connected together.

20. The lancing device of claim 13, in which the second housing comprises a unitary member connected to a positioning band coupled to the first housing, the second housing having at least one groove that extends through the unitary member along the longitudinal axis to allow communication from the inside of the second housing to the inside of the first housing.

21. The lancing device of claim 20, in which the moveable member comprises at least one return arm that extends through the groove so that the moveable member is guided by the at least one return arm along a path defined by the at least one groove.

22. The lancing device of claim 13, further comprising a second bias member configured to bias the moveable member in a direction towards the proximal end.

23. The lancing device of claim 22, in which the second bias member comprises a resilient member disposed outside the second housing and connected to the at least one return arm.

24. The lancing device of claim 22, in which the second bias member comprises a helical spring.

25. A lancing device comprising:
a first housing having spaced apart proximal and distal ends disposed along a longitudinal axis;
a second housing disposed in the first housing in a fixedly attached to the first housing;
a movable member disposed in the second housing and configured for movement along the longitudinal axis, the moveable member includes a plurality of arms extending away from the longitudinal axis towards the distal end;
a lancet having a body and a projection extending from the body of the lancet, the body of the lancet capable of being disposed in a volume defined by the plurality of arms of the moveable member; and
a collet mounted on the plurality of arms for movement of the collet along the longitudinal axis on the plurality of arms from a first position of the collet in which the plurality of arms constrains the body of the lancet from movement and a second position of the collet in which the body of the lancet is not constrained by the plurality of arms.

26. The lancing device of claim 25, further comprising:
a first bias member located in the housing to bias the moveable member in a direction towards the distal end;
a first actuator coupled to the movable member so that the movable member is positioned proximate the proximal end in a primed-position; and
a second actuator carried on a portion of the first actuator, the second actuator configured to allow the movable member to move from the primed-position to a position proximate the distal end.

27. The lancing device of claim 26, further comprising:
a lancet ejection mechanism including:
a third actuator mounted to the housing, the third actuator being disposed in:
a first position in which the third actuator is disengaged from both the lancet depth adjustment member and the moveable member, and
a second position in which the third actuator is connected to the moveable member with the depth adjustment member in a specific position so that a portion of the third actuator is displaced partially in a groove formed on a circumferential portion of the depth adjustment member to move the moveable member towards the distal end to eject the lancet.

28. The lancing device of claim 27, further comprising:
a collar disposed between the depth adjustment member and the collet, the collar configured to prevent movement of the collet towards the distal end.

29. The lancing device of claim 28, further comprising a cap to cover an aperture in which the lancet can extend from the depth adjustment member, the cap being connected to the depth adjustment member.

30. The lancing device of claim 27, further comprising a third bias member coupled to the moveable member to bias the collet in a direction towards the distal end.

31. The lancing device of claim 27, in which the first bias member comprises a resilient member in contact with the moveable member.

32. The lancing device of claim 25, in which the first housing comprises two halves connected together.

33. The lancing device of claim 25, wherein the second housing comprising a unitary member connected to a positioning band coupled to the first housing, the second housing having at least one groove that extends through the unitary member along the longitudinal axis to allow communication from the inside of the second housing to the inside of the first housing.

34. The lancing device of claim 33, further comprising a second bias member configured to bias the moveable member in a direction towards the proximal end.

35. The lancing device of claim 34, in which the moveable member comprises at least one return arm that extends through the groove so that the moveable member is guided by the at least one return arm along a path defined by the at least one groove.

36. The lancing device of claim 35, in which the second bias member comprises a resilient member disposed outside the second housing and connected to the at least one return arm.

37. The lancing device of claim 34, in which the second bias member comprises a helical spring.

* * * * *